United States Patent
Zhu et al.

(10) Patent No.: US 9,951,097 B2
(45) Date of Patent: Apr. 24, 2018

(54) ANTIBACTERIAL COMPOUNDS TARGETING ISOPRENOID BIOSYNTHESIS

(71) Applicants: THE BOARD OF TRUSTEES OF THE UNIVERSITY OF ILLINOIS, Urbana, IL (US); THE REGENTS OF THE UNIVERSITY OF CALIFORNIA, La Jolla, CA (US)

(72) Inventors: Wei Zhu, Urbana, IL (US); Steffen Lindert, San Diego, CA (US); Yonghui Zhang, Beijing (CN); William Sinko, La Jolla, CA (US); Kai Li, Urbana, IL (US); James Andrew McCammon, La Jolla, CA (US); Eric Oldfield, Champaign, IL (US)

(73) Assignees: The Board of Trustees of the University of Illinois, Urbana, IL (US); The Regents of the University of California, Oakland, CA (US)

( * ) Notice: Subject to any disclaimer, the term of this patent is extended or adjusted under 35 U.S.C. 154(b) by 36 days.

(21) Appl. No.: 14/649,153

(22) PCT Filed: Dec. 4, 2013

(86) PCT No.: PCT/US2013/073148
§ 371 (c)(1),
(2) Date: Jun. 2, 2015

(87) PCT Pub. No.: WO2014/089226
PCT Pub. Date: Jun. 12, 2014

(65) Prior Publication Data
US 2016/0039857 A1 Feb. 11, 2016

Related U.S. Application Data

(60) Provisional application No. 61/733,141, filed on Dec. 4, 2012.

(51) Int. Cl.
| | |
|---|---|
| C07H 15/26 | (2006.01) |
| A61K 31/4178 | (2006.01) |
| A61K 31/506 | (2006.01) |
| A61K 31/551 | (2006.01) |
| A61K 31/7034 | (2006.01) |
| C07H 15/203 | (2006.01) |
| A61K 31/167 | (2006.01) |
| A61K 31/4439 | (2006.01) |
| C07D 233/24 | (2006.01) |
| C07D 239/06 | (2006.01) |
| C07D 239/28 | (2006.01) |
| C07D 243/04 | (2006.01) |
| C07D 209/08 | (2006.01) |
| A61K 31/43 | (2006.01) |
| A61K 31/7056 | (2006.01) |

(52) U.S. Cl.
CPC ............ *C07H 15/26* (2013.01); *A61K 31/167* (2013.01); *A61K 31/4178* (2013.01); *A61K 31/43* (2013.01); *A61K 31/4439* (2013.01); *A61K 31/506* (2013.01); *A61K 31/551* (2013.01); *A61K 31/7034* (2013.01); *A61K 31/7056* (2013.01); *C07D 209/08* (2013.01); *C07D 233/24* (2013.01); *C07D 239/06* (2013.01); *C07D 239/28* (2013.01); *C07D 243/04* (2013.01); *C07H 15/203* (2013.01)

(58) Field of Classification Search
CPC ........ C07H 15/26; C07H 5/203; A61K 31/43; A61K 31/4178; A61K 31/7056; A61K 31/506; A61K 31/551; A61K 31/7034; C07D 233/24; C07D 239/06; C07D 243/04
USPC .......................... 514/25, 197, 218; 536/16.8
See application file for complete search history.

(56) References Cited

U.S. PATENT DOCUMENTS

| | | | |
|---|---|---|---|
| 5,972,933 | A | 10/1999 | Pfirrmann |
| 6,638,979 | B1 | 10/2003 | Riebel et al. |
| 2005/0208639 | A1 | 9/2005 | Ammirati et al. |
| 2012/0115877 | A1 | 5/2012 | Scott et al. |

FOREIGN PATENT DOCUMENTS

| | | | |
|---|---|---|---|
| GB | 1007334 | A | 10/1961 |
| GB | 1007334 | * | 10/1965 |
| WO | 2011026107 | A1 | 3/2011 |

OTHER PUBLICATIONS

Ozden et al. (Bioorganic & Medicinal Chemistry 13(2005) 1587-1597).*
PisKov et al. (Khimiko-Farmatsevticheskii Zhurnal (1974), 8(6), 17-20) (abstract sent).*
"International Search Report and Written Opinion," for PCT/US 2013/073148 filed Dec. 4, 2013, 13 pp.
Butler et al., "Comparative In Vitro Activity Profiles of Novel Bis-Indole Antibacterials against Gram-Positive and Gram-Negative Clinical Isolates," Antimicrobial Agents and Chemotherapy, Sep. 2010. 54: pp. 3974-3977.

(Continued)

*Primary Examiner* — Shaojia Anna Jiang
*Assistant Examiner* — Michael C Henry
(74) *Attorney, Agent, or Firm* — Haukaas Fortius PLLC; Michael H. Haukaas

(57) ABSTRACT

With the rise in resistance to antibiotics such as methicillin, there is a need for new drugs. The invention provides small molecules that inhibit cellular drug targets such as UPPS and FPPS by interacting with binding pockets, thereby preventing enzyme function. Compounds described herein are also active against *Staphylococcus aureus* (MIC90~0.25 μg/mL), can potently synergize with methicillin (fractional inhibitory concentration index=0.25), and are protective in a mouse infection model. The invention therefore provides numerous compounds for anti-bacterial treatments and for restoring sensitivity to drugs such as methicillin, using combination therapies.

2 Claims, 19 Drawing Sheets

(56) References Cited

OTHER PUBLICATIONS

Durrant et al., "Non-Bisphosphonate Inhibitors of Isoprenoid Biosynthesis Identified via Computer-Aided Drug Design," Chem. Biol. Drug. Des., Jun. 2011. 78: pp. 323-332.

Guo et al., "Bisphosphonates target multiple sites in both cis- and trans-prenyltransferases," PNAS, Jun. 12, 2007. 104: pp. 10022-10027.

Jahnke et al., "Allosteric non-bisphosphonate FPPS inhibitors identified by fragment-based discovery," Nature Chemical Biology, Sep. 2010. 6: pp. 660-666.

Larsen et al., "Discovery and initial development of a novel class of antibacterials: Inhibitors of *Staphylococcus aureus* transcription/translation," Bioorganic & Medicinal Chemistry Letters, Oct. 2006. 16: pp. 6173-6177.

Lindert et al., "Farnesyl Diphosphate Synthase Inhibitors from In Silico Screening," Chem Biol Drug Des, Feb. 2013. 81: pp. 742-748.

Mott et al., "Resistance mapping and mode of action of a novel class of antibacterial anthranilic acids: evidence for disruption of cell wall biosynthesis," Journal of Antimicrobial Chemotherapy, Jun. 2008. 62: pp. 720-729.

Oldfield, "Targeting Isoprenoid Biosynthesis for Drug Discovery: Bench to Bedside," American Chemical Society, Mar. 2010. 30: pp. A-K.

Panchal et al., "Novel Broad-Spectrum Bis-(Imidazolinylindole) Derivatives with Potent Antibacterial Activities against Antibiotic-Resistant Strains," Antimicrobial Agents and Chemotherapy, Oct. 2009. 53: pp. 4283-4291.

Peukert et al., "Design and structure-activity relationships of potent and selective inhibitors of undecaprenyl pyrophosphate synthase (UPPS): Tetramic, tetronic acids and dihydropyridin-2-ones," Bioorganic & Medicinal Chemistry Letters, Feb. 2008. 18: pp. 1840-1844.

Teng et al., "Structures, mechanisms and inhibitors of undecaprenyl diphosphate synthase: a cis-prenyltransferase for bacterial peptidoglycan biosynthesis," Bioorganic Chemistry, Jan. 2012. 43: pp. 51-57.

Yang et al., "Mechanism of a prototypical synthetic membrane-active antimicrobial: Efficient hole-punching via interaction with negative intrinsic curvature lipids," PNAS, Dec. 30, 2008. 105: pp. 20595-20600.

Zhu et al., "Antibacterial drug leads targeting isoprenoid biosynthesis," PNAS, Jan. 2, 2013. 110: pp. 123-128.

\* cited by examiner

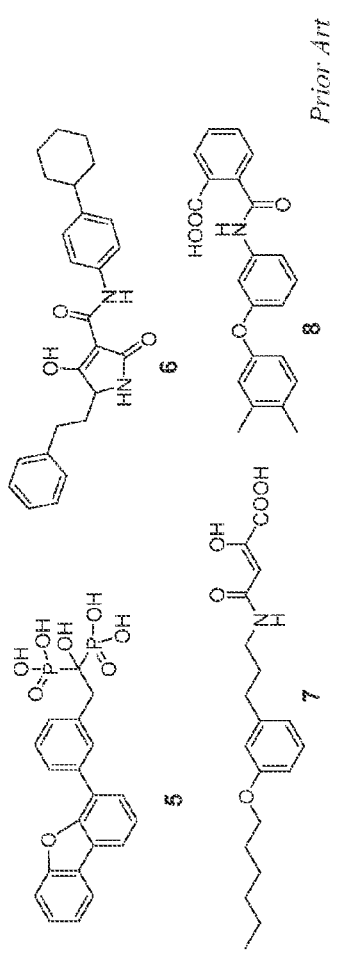
*Figure 2* — Prior Art
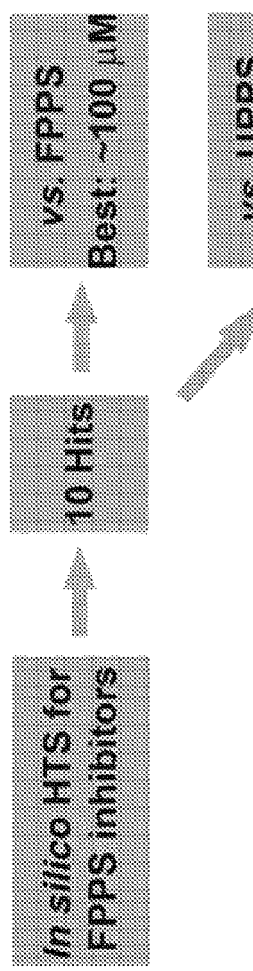
*Figure 3*

Table 2. Data collection and refinement statistics for *E. coli* UPPS

| Crystals | EcUPPS/8 (3SGT) | EcUPPS/9 (3SGV) | EcUPPS/10 (3SGX) | EcUPPS/11 (3HSO) | EcUPPS/12 (4H2O) |
|---|---|---|---|---|---|
| Data collection | | | | | |
| Space group | $P2_12_12_1$ | $P2_12_12_1$ | $P2_12_12_1$ | $P2_12_12_1$ | $P2_12_12_1$ |
| Unit cell dimension (Å) | | | | | |
| $a, b, c$ (Å) | 62.92, 68.35, 111.98 | 63.14, 69.00, 112.56 | 60.95, 68.14, 111.61 | 62.77, 68.72, 112.06 | 63.38, 68.37, 109.94 |
| X-ray source | APS 21-ID-G | APS 21-ID-F | APS 21-ID-F | APS 21-ID-D | APS 21-ID-F |
| Wavelength (Å) | 0.97857 | 0.97857 | 0.97857 | 0.97857 | 0.97857 |
| Resolution (Å)* | 50.0-1.85 (1.88-1.85) | 50.0-1.61 (1.64-1.61) | 50.0-2.45 (2.49-2.45) | 50.0-1.84 (1.87-1.84) | 50.0-2.14 (2.18-2.14) |
| No. of reflection observed | 348,506 | 956,565 | 98,722 | 423,643 | 371,965 |
| Unique | 41,827 (1,909) | 62,778 (2,554) | 17,225 (786) | 42,560 (1,870) | 26,986 (1319) |
| Completeness (%) | 99.5 (93.4) | 97.6 (80.5) | 96.9 (90.7) | 99.3 (89.2) | 99.7 (99.4) |
| R-merge | 0.067 (0.502) | 0.095 (0.704) | 0.092 (0.451) | 0.065 (0.642) | 0.082 (0.594) |
| I/σ(I) | 41.7 | 35.4 | 23.4 | 28.9 | 30.7 |
| Multiplicity | 8.3 (5.1) | 15.2 (5.6) | 5.7 (4.7) | 10.0 (5.3) | 13.8 (13.5) |
| Refinement statistics | | | | | |
| Resolution range (Å) | 35.68-1.85 | 43.61-1.61 | 32.65-2.45 | 35.71-1.84 | 46.48-2.14 |
| R-work/R-free (%) | 17.4/22.7 | 17.4/21.4 | 24.2/32.8 | 16.8/21.1 | 23.2/29.5 |
| RMSD | | | | | |
| Bond lengths | 0.024 | 0.026 | 0.015 | 0.024 | 0.017 |
| Bond angles | 1.851 | 2.249 | 1.682 | 1.901 | 1.92 |
| No. of atoms | | | | | |
| Protein | 3,413 | 3,487 | 3,256 | 3,397 | 3,217 |
| Ligand | 27 | 135 | 68 | 69 | 96 |
| B average (Å²) of protein | 32.30 | 25.21 | 46.07 | 30.54 | 38.76 |
| B average (Å²) of ligand | 37.25 | 33.60 | 59.17 | 41.17 | 74.15 |

*Values in the parentheses are for the highest resolution shells.

*Figure 6*

Table 2 (*Continued*). Data collection and refinement statistics for *E. coli* UPPS

| Crystals | EcUPPS/13 (4H38) | EcUPPS/14 (4H3C) | EcUPPS/15 (4H3A) | EcUPPS/16 (4H2J) | EcUPPS/18 (4H2M) |
|---|---|---|---|---|---|
| Data collection | | | | | |
| Space group | $P2_12_12_1$ | $P2_12_12_1$ | $P2_12_12_1$ | $P2_12_12_1$ | $P2_12_12_1$ |
| Unit cell dimension (Å) | | | | | |
| $a, b, c$ (Å) | 63.26, 68.82, 111.49 | 63.33, 69.10, 111.69 | 62.98, 68.71, 111.92 | 68.16, 68.96, 111.74 | 62.83, 68.89, 112.02 |
| X-ray source | APS 21-ID-F | APS 21-ID-G | APS 21-ID-G | APS 21-ID-F | APS 21-ID-G |
| Wavelength (Å) | 0.97857 | 0.97857 | 0.97857 | 0.97857 | 0.97857 |
| Resolution (Å) | 50.0-1.95 (1.98-1.95) | 50.0-1.93 (1.96-1.93) | 50.0-1.98 (2.01-1.98) | 50.0-1.81 (1.84-1.81) | 50.0-1.78 (1.81-1.78) |
| No. of reflection observed | 262,481 | 542,651 | 493,329 | 396,626 | 375,414 |
| Unique | 36,240 (1,786) | 37,169 (1,846) | 34,503 (1,700) | 45,055 (2,204) | 47,258 (2,312) |
| Completeness (%) | 99.8 (100.0) | 99.3 (99.1) | 100.0 (100.0) | 99.6 (100.0) | 99.9 (98.8) |
| R-merge | 0.091 (0.642) | 0.083 (0.637) | 0.059 (0.635) | 0.076 (0.698) | 0.066 (0.670) |
| $I/\sigma(I)$ | 20.4 | 34.2 | 39.7 | 27.8 | 29.1 |
| Multiplicity | 7.2 (7.4) | 14.6 (14.4) | 14.3 (14.2) | 8.8 (9.0) | 7.9 (6.3) |
| Refinement statistics | | | | | |
| Resolution range (Å) | 34.41-1.95 | 43.43-1.93 | 46.43-1.98 | 30.39-1.81 | 43.46-1.78 |
| R-work/R-free (%) | 20.6/26.2 | 20.6/25.0 | 20.9/24.9 | 19.7/23.4 | 20.4/24.2 |
| RMSD | | | | | |
| Bond lengths | 0.020 | 0.022 | 0.019 | 0.023 | 0.024 |
| Bond angles | 1.953 | 2.092 | 1.855 | 2.262 | 2.116 |
| No. of atoms | | | | | |
| Protein | 3,324 | 3,257 | 3,211 | 3,360 | 3,353 |
| Ligand | 28 | 75 | 46 | 74 | 60 |
| B average (Å$^2$) of protein | 28.91 | 33.39 | 39.08 | 28.08 | 29.14 |
| B average (Å$^2$) of ligand | 68.04 | 58.51 | 69.71 | 53.85 | 63.86 |

*Values in the parentheses are for the highest resolution shells.

*Figure 6 (cont.)*

SEQUENCE LISTING

<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
cgcgaattcg cg                                                        12

<210> SEQ ID NO 2
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gtattgaggg tcgcatgttt aaaaagctaa taaataaaaa gaacac                   46

<210> SEQ ID NO 3
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaggagagt tagagcccta ctcctcactc                                       30
```

ANTIBACTERIAL COMPOUNDS TARGETING ISOPRENOID BIOSYNTHESIS

RELATED APPLICATIONS

This application is a National Stage filing under 35 U.S.C. § 371 of International Application No. PCT/US2013/073148, filed Dec. 4, 2013, which claims priority under 35 U.S.C. § 119(e) to U.S. Provisional Patent Application No. 61/733,141, filed Dec. 4, 2012, which applications are incorporated herein by reference.

GOVERNMENT SUPPORT

This invention was made with government support under Contract Nos. GM31749 and 5R01AI074233-16, both awarded by the National Institutes of Health, and MCB-1020765 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Oct. 13, 2015, is named 500.017US1_SL.txt and is 1,140 bytes in size.

BACKGROUND OF THE INVENTION

Targeting isoprenoid biosynthesis is a potentially important route for antibiotic discovery because isoprenoids are involved in the very early steps of bacterial cell wall biosynthesis, including the condensation of dimethylallyl diphosphate (DMAPP, 1) with two molecules of isopentenyl diphosphate (IPP, 2) to form farnesyl diphosphate (FPP, 3), catalyzed by the enzyme farnesyl diphosphate synthase (FPPS), followed by the addition of 8 more IPP molecules to form undecaprenyl diphosphate (UPP, 4); FIG. 1. Formation of UPP (4) is catalyzed by the enzyme undecaprenyl diphosphate synthase (UPPS), and several moderate UPPS inhibitors are known. UPP is then hydrolyzed to the monophosphate, which is next converted to Lipid I and Lipid II, leading to formation of cell wall peptidoglycan; FIG. 1.

The UPPS structure is unusual in that there are four known ligand binding sites, opening up the possibility of designing a diverse range of inhibitors. UPPS inhibitors could act synergistically with cell wall biosynthesis inhibitors to reduce the toxicity of drugs such as vancomycin (by decreasing dosage), or to restore drug sensitivity (e.g., with methicillin-resistant *Staphylococcus aureus* (MSRA)). Antibiotics such as methicillin and vancomycin act in the latter stages of peptidoglycan formation, as shown in FIG. 1. However, new UPPS inhibitors are needed because UPPS is an essential microbial enzyme not present in humans.

SUMMARY

With the rise in resistance to antibiotics such as methicillin, there is a need for new therapeutic agents and drugs. This disclosure reports the discovery and x-ray crystallographic structures of several chemically diverse compounds (e.g., bisamidines) that inhibit bacterial undecaprenyl diphosphate synthase (UPPS), an essential enzyme involved in cell wall biosynthesis. The inhibitors bind to one or more of the four UPPS inhibitor-binding sites identified previously, with the most active compounds binding to site 4, outside the catalytic center. The most potent leads are active against *Staphylococcus aureus* ($MIC_{90}$~0.25 µg/mL) and one potently synergizes with methicillin (fractional inhibitory concentration index=0.25) and is protective in a mouse infection model. These results provide numerous new leads for anti-bacterial development and open up the possibility of restoring sensitivity to drugs such as methicillin, using combination therapies.

The invention thus provides a compound, such as a bisphenylamidine or bisphenylalkyne compound, that includes (a) two moieties of Formula I:

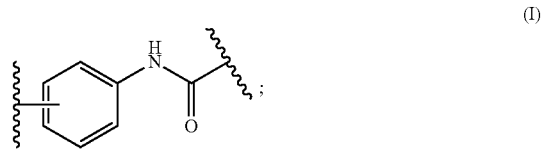

or (b) two moieties of Formula II:

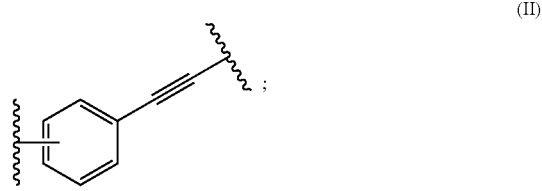

wherein the moieties of Formula I are connected by a linker at the amide carbonyl, or the moieties of Formula II are connected by a linker at the distal carbon of the phenylalkyne. Each phenyl of Formula I or Formula II can be optionally substituted. Each moiety of Formula I or Formula II includes at least one heterocycle or imidamide substituent, optionally linked to the Formula I or Formula II moiety through a linker (e.g., a ($C_1$-$C_6$)alkyl or other linker described herein). The compound can have a molecular weight of at least about 300 and less than about 1,200.

The compound can be a potent undecaprenyl diphosphate synthase (UPPS) inhibitor, for example, where the inhibitor binds to at least site 4 of the UPPS. In some embodiments, the compound does not bind to site 1 of UPPS. In various embodiments, the compound additionally binds to site 1, site 2, or site 3, or a combination thereof, of UPPS. The compound can inhibit UPPS with an $IC_{50}$ value of less than about 1 µM, less than about 0.5 µM, less than about 400 nM, or less than about 150 nM. The compound can inhibit the activity of farnesyl diphosphate synthase (FPPS) and/or another prenyltransferase. The compound can also kill or inhibit the growth of MRSA cells or related infections.

The invention also provides a method of inhibiting a prenyltransferase enzyme comprising contacting the enzyme with an effective amount of a compound described herein. The invention further provides a method of killing or inhibiting the growth of bacteria comprising contacting the bacteria with an effective amount of a compound described herein.

In some embodiments, the compounds inhibit the activity of UPPS, FPPS and/or other prenyltransferases. In various embodiments, the small molecule compounds can inhibit the cellular drug targets UPPS and FPPS by interacting with binding pockets, thereby preventing enzyme function.

The invention further provides methods for the treatment of a bacterial infection, such as a methicillin-resistant *Staphylococcus aureus* (MRSA) infection or a vancomycin-resistant *Enterococcus faecalis* (VRE) infection. The invention also provides methods for killing or inhibiting the growth of bacteria, including antibiotic-resistant bacteria. Strains of antibiotic-resistant bacteria are known in the art and are discussed in, for example, U.S. Pat. No. 5,972,933 (Pfirrmann), and the compounds described herein can be used in combination with a second antibiotic (e.g., methicillin or vancomycin) wherein the bacteria is resistant to the second antibiotic, to overcome the resistance of the bacteria to the second antibiotic. The antibiotic compounds can be administered to a bacteria, or a mammal infected with a bacteria in need of therapy, separately or together in a single dosage.

The invention therefore provides novel compounds of the formulas described herein, intermediates for the synthesis of compounds of the formulas described herein, as well as methods of preparing compounds of the formulas described herein. The invention also provides compounds of the formulas described herein that are useful as intermediates for the synthesis of other useful compounds. The invention provides for the use of compounds of the formulas described herein for the manufacture of medicaments useful for the treatment of bacterial infections in a mammal, such as a human. A compound described herein can also be prepared in a pharmaceutical composition. Such compositions can include, for example, a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 2. Chemical structures of various known UPPS inhibitors.

FIG. 3. Schematic illustration of hit-to-lead development. FPPS inhibitors obtained by in silico screening of the NCI diversity set II were screened against *E. coli* UPPS basically as described previously (see Durrant et al., *Chem Biol Drug Des* 2011, 78(3):323-332): the most potent hit (~5 µM) was then used as a reference for a similarity search using Scifinder software. Twenty-two compounds suggested were obtained from the NIH Developmental Therapeutics Program. The most active lead was found to have ~110 nM $IC_{50}$ values against both *E. coli* UPPS and *S. aureus* UPPS.

FIG. 6. Data collection and refinement statistics for *E. coli* UPPS; summarized as Table 2.

DETAILED DESCRIPTION

Figure 1:
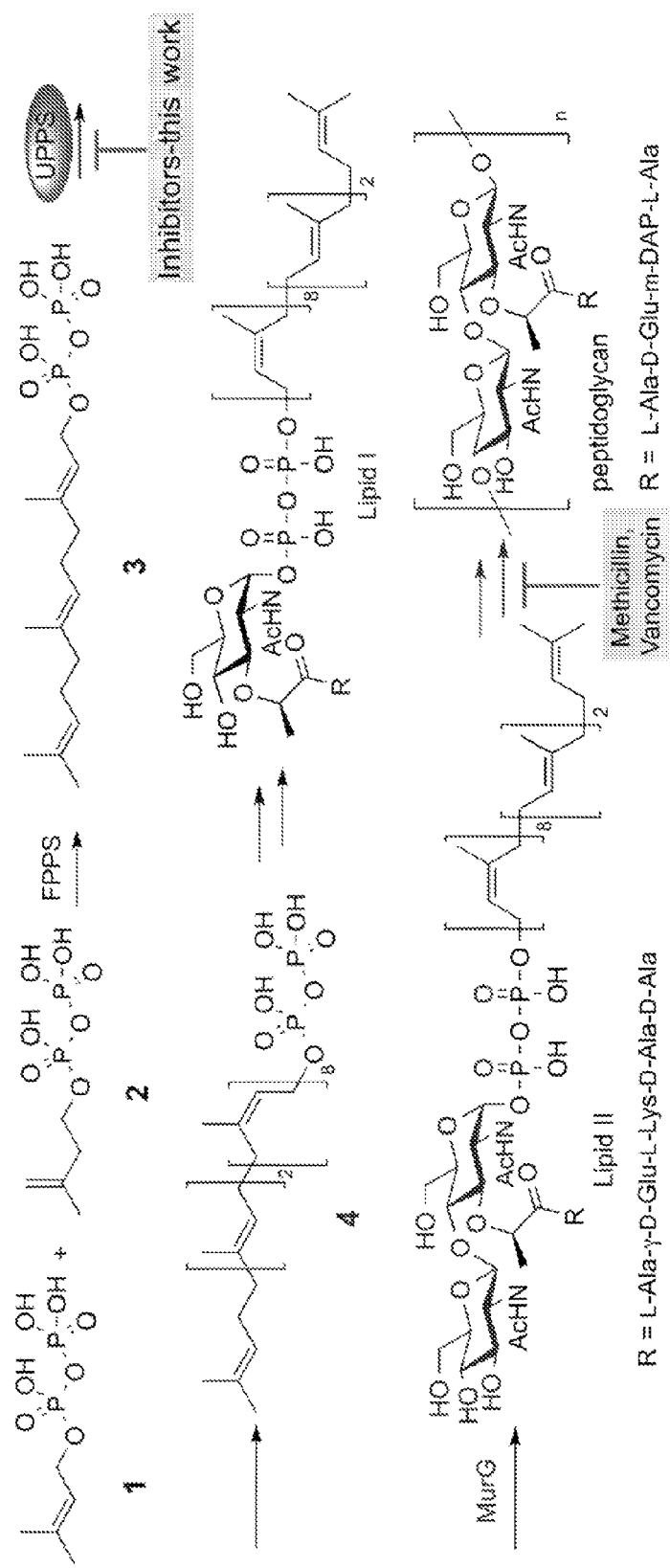
FIG. 1. Schematic outline of cell wall biosynthesis (in most bacteria) showing involvement of isoprenoid biosynthesis in the early stages of peptidoglycan formation.

Certain drugs target isoprenoid biosynthesis. There is much interest in targeting enzymes involved in isoprenoid biosynthesis for use as anti-infective and anti-cancer agents. Undecaprenyl diphosphate synthase (UPPS) is present in *Plasmodium falciparum* and *S. aureus* and is a verified drug target of interest. Compounds that inhibit UPPS are of significant interest to pharmaceutical companies and researchers developing anti-infective drugs. The enzyme farnesyl diphosphate synthase (FPPS) has been identified as an interesting target for antitumor and antimicrobial treatment. Additionally it has pharmaceutical importance in the treatment of malignant bone disease.

In various embodiments, the compounds described herein are not bisphosphonates, nor are they tetramic acids, both of which have problems with distribution about the body. Various genera and examples of the compounds are novel, and to the best of our knowledge not described as inhibitors of UPPS or FPPS anywhere in the literature. Additionally, some compounds are high affinity (in the nanomolar $IC_{50}$ range), are effective in cellular assays, and are effective in animal models of MRSA infections. The compounds are therefore important leads for drug development.

Several of the compounds described herein have been tested via inhibition assays against UPPS and FPPS with favorable results, and many have been crystallized bound to the protein. Additionally, some compounds have been tested and have demonstrated effectiveness in cellular assays of bacterial cell growth, and in animal models of methicillin resistant bacterial infections.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

The term "amide" refers to a —C(=O)—NH$_2$ group. The term "alkylamide" refers to a —C(=O)—NH(alkyl) group. The term "phenylamidine" refers to a -Ph-(dihydroimidazole) group, a -Ph-(dihydropyrimidine) group, or a -Ph-(tetrahydropyrimidine) group, each of which imidazoles and pyrimidines are nitrogen heterocycles.

The term "amidine" refers to a moiety of the formula —C(=NR)—NR$_2$, where each R is independently H, alkyl, or part of a carbon chain. When an amidine is a substituent, it can be referred to as an imidamide substituent. Imidamides are well known in the art and are further described by, for example, U.S. Pat. No. 6,638,979 (Riebel et al.).

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, βcarbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl, and dimers thereof. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, silicon, and sulfur, and optionally substituted with one or more groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, dihydropyrimidine, tetrahydropyrimidine, and thiomorpholine. A 2H-pyran can be an oxygen-linked tetrahydropyranyl group such as a saccharide or "sugar" moiety, where the tetrahydropyran is substituted by two, three, or four substituents, as defined below, such as hydroxy and/or amino groups.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like. Various combinations of the aforementioned positions are included in the compounds described herein.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl. Various combinations of the aforementioned positions are included in the compounds described herein.

An "alkylene" refers to a saturated, branched or straight chain hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like. The alkynyl can be unsubstituted or substituted.

An "alkenylene" refers to an unsaturated, branched or straight chain hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—). The alkenylene can be unsubstituted or substituted.

A "linker" or "linking group" refers to an organic or inorganic chain or moiety that connects to other groups of a molecule. A linker can be, for example, a group L where L is a an alkylene, an alkenylene, an aryl diradical, a direct bond or a divalent radical of the formula —W—Z—W—; where each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, —(CX*$_2$)—, —(CH$_2$)$_n$—(CX*$_2$)— where n is 1-3, or a direct bond; and Z is a divalent moiety selected from ($C_1$-$C_{12}$)alkyl, ($C_2$-$C_{12}$)alkenyl, ($C_2$-$C_{12}$)alkynyl, ($C_3$-$C_8$)cycloalkyl, ($C_6$-$C_{10}$)aryl, —N(R')C(=O)—, —C(=O)N(R')—, —OC(=O)—, —C(=O)O—, —N(R')—, —C(=O)—, —(CX*$_2$)—, —(CH$_2$)$_n$—(CX*$_2$)— where n is 1-3, —(OCH$_2$—CH$_2$)$_n$— where n is 1 to about 10, —C(O)NH(CH$_2$)$_n$— where n is 1 to about 6, —OP(O)(OH)O—, —OP(O)(OH)O(CH$_2$)$_n$— where n is 1 to about 6, —OP(O)(OH)OCH$_2$CH(OH)CH$_2$—, —N$^+$(Me)$_2$(CH$_2$)$_n$— where n is 1 to about 6; or ($C_1$-$C_{12}$)alkyl, ($C_2$-$C_{12}$)alkenyl, ($C_2$-$C_{12}$)alkynyl, or —(OCH$_2$—CH$_2$)$_n$— optionally interrupted between two carbons, or between a carbon and an oxygen, with a ($C_3$-$C_8$)cycloalkyl, heteroaryl, heterocycle, or ($C_6$-$C_{10}$)aryl group, where n is 1 to about 6; or Z is a direct bond.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure, and combinations thereof. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NHR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(=S)NRR, —C(=NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

As to any of compound described herein, which contains one or more substituents, it is understood, of course, that such groups do not contain any substitution or substitution patterns that are sterically impractical and/or synthetically non-feasible. The total molecular weight of substituents on a single group will typically be less than about 600, 500, 400, 300, 200, or 100. It will be appreciated that the compounds of the invention can contain asymmetrically substituted carbon atoms, and may be isolated in optically active or racemic forms. It is well known in the art how to prepare optically active forms, such as by resolution of racemic forms or by synthesis from optically active starting materials or by the use of enantioselective catalytic reactions. All chiral, diastereomeric, racemic forms and all geometric isomeric forms of a compound are intended as part of this invention.

Methods for analyzing and determining the inhibition of enzymes are well known and are described in, for example, U.S. Patent Publication No. 2012/0196835 (Oldfield et al.).

Compounds and Methods

As described above, the invention provides various compounds, such as bisphenylamidine or bisphenylalkyne compounds, that include (a) two moieties of Formula I:

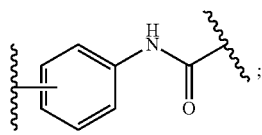

(I)

or (b) two moieties of Formula II:

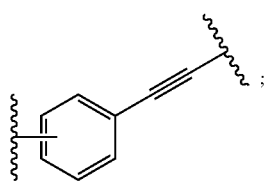

(II)

wherein the moieties of Formula I are connected by a linker at the amide carbonyl, or the moieties of Formula II are connected by a linker at the distal carbon of the phenylalkyne. Such linkers can be, for example, a divalent phenyl or biphenyl moiety, wherein the aryl rings are optionally substituted. Each moiety of Formula I or Formula II includes at least one heterocycle, imidamide, or amine substituent, optionally linked to the Formula I or Formula II moiety through a linker (e.g., a a $(C_1-C_6)$alkyl).

The compound can have a molecular weight of at least about 250, least about 300, least about 350, least about 400, least about 500, least about 600, least about 700, or least about 750. Such compounds can also have molecular weights of less than about 1,500, less than about 1,200, less than about 1,000, less than about 900, less than about 800, less than about 750, less than about 700, less than about 650, less than about 600, or less than about 500.

The linker can be a variety of groups, such as an aryl, heteroaryl, or alkylene that optionally includes an alkylene or alkenylene in the linker. The linker can be optionally substituted. Examples of some specific linkers, which can optionally be substituted, include phenyl, biphenyl, pyridyl, bipyridyl, pyrimidinyl, naphthyl, fluorene, carbazole, dibenzofuran, dibenzothiophene, dibenzothiophene 5,5-dioxide, diphenyl ether, 1,3-diphenylurea, vinylbenzene, divinylbenzene, phenylethyl, and ethyl.

In some embodiments, the compound is a compound of Formula III:

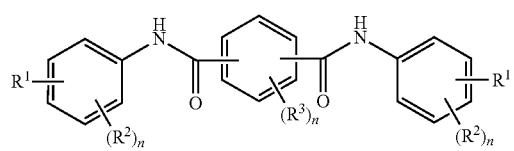

(III)

wherein
each $R^1$ is independently an oxygen heterocycle, a nitrogen heterocycle or an imidamide;
each $R^2$ is independently hydrogen, amide, alkylamide, or a nitrogen heterocycle optionally linked by a phenyl, urea, or phenylurea;
each $R^3$ is independently hydrogen, alkyl, alkoxy, hydroxy, amino, nitro, halo, or an optionally substituted phynylamide; and
each n is independently 1 or 2; or a salt or solvate thereof.

In other embodiments, the compound is a compound of Formula IV:

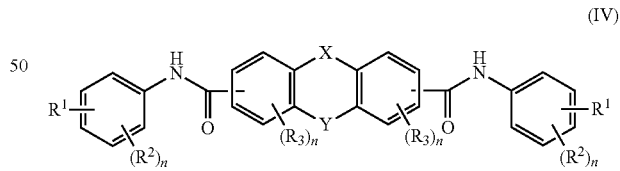

(IV)

wherein
X is $CH_2$, O, NH, S, $SO_2$, NH—(C=O)—NH, a direct bond, or absent;
Y is $CH_2$, O, NH, S, $SO_2$, a direct bond, or absent;
each $R^1$ is independently an oxygen heterocycle, a nitrogen heterocycle or an imidamide;
each $R^2$ is independently hydrogen, amide, alkylamide, or a nitrogen heterocycle optionally linked by a phenyl, urea, or phenylurea;
each $R^3$ is independently hydrogen, alkyl, alkoxy, hydroxy, amino, nitro, halo, or an optionally substituted phenylamide; and each n is independently 1 or 2; or a salt or solvate thereof.

When X and Y are both absent, the result is the presence of a naphthalene moiety (i.e., fused benz moieties, as in structure IV.4 below).

Specific values for $R^1$ include monosaccharide (e.g., glucose or aminoglucose), tetrahydropyran, imidazole, dihydroimidazole, 4-methyldihydroimidazole, or —C(=NH)NHMe.

Specific values for $R^2$ include H, —C(=O)NH$_2$, —C(=O)NHMe, imidazole, or dihydroimidazole.

Specific values for $R^3$ include H, Me, Et, OMe, OEt, OH, NH$_2$, NO$_2$, F, Cl, Br, or —C(=O)NH—Ph-dihydroimidazole.

In one embodiment, the compound is a bisphenylalkyne of Formula V:

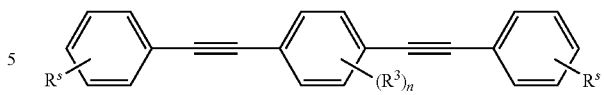

(V)

wherein
each $R^s$ is independently a saccharide moiety, such as an aminosugar;
each $R^3$ is independently hydrogen, alkyl, alkoxy, hydroxy, amino, nitro, halo, or an optionally substituted phenylamide; and
n is independently 1, 2, 3, or 4;
or a salt or solvate thereof.

In one embodiment, the compound of Formula V is a bisphenylalkyne having the structure:

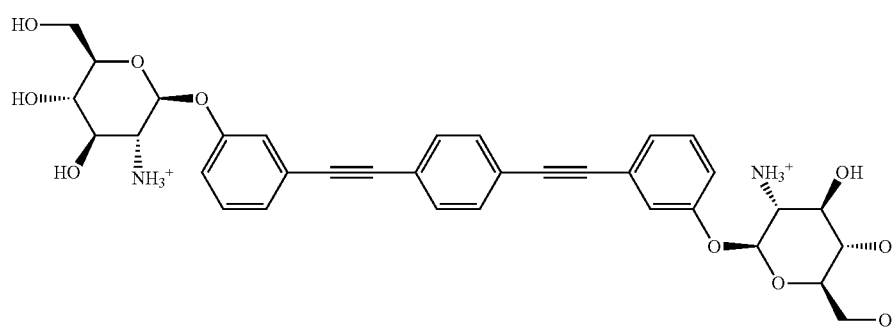

(V.1)

or a salt or solvate thereof. In some embodiments, one or more of the phenyl rings can be substituted with one, two, three, or four $R^2$ or $R^3$ groups, where $R^2$ and $R^3$ are as defined above. The saccharide moieties of Formula V any known sugar, aminosugar, or iminosugar, and the sugar moieties can be optionally protected (e.g., on O or N) with one or more protecting groups. Similar modifications can be made to other phenyl moieties and sugar moieties described herein.

In some embodiments, the compound that includes two moieties of Formula I or Formula II can be:

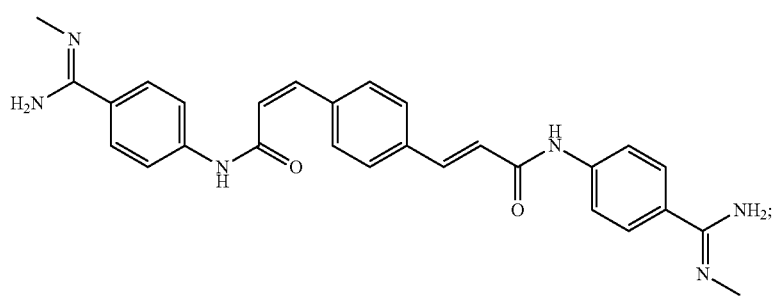

(X.1)

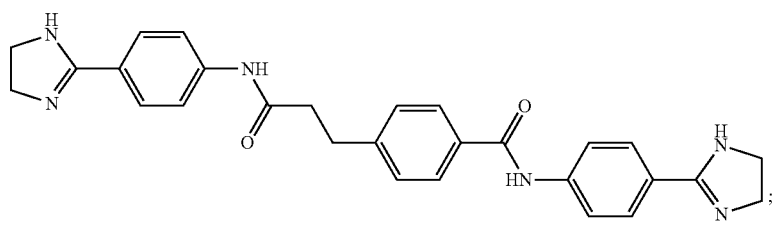

(X.2)

(X.3)
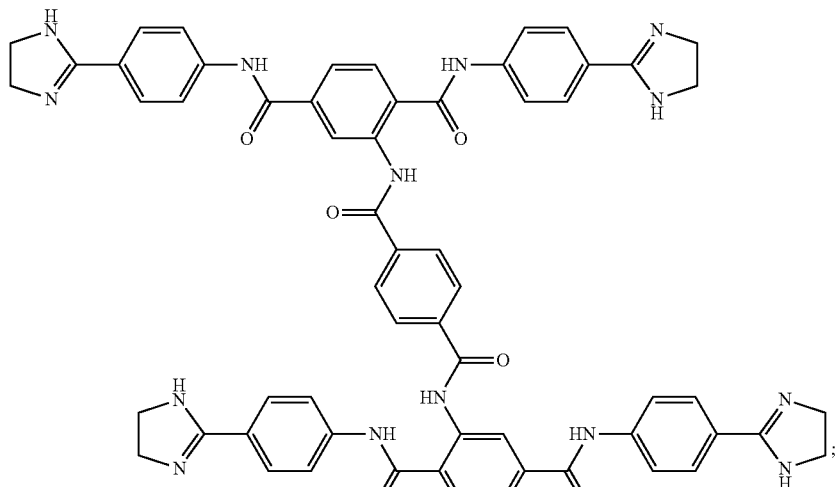
(X.4)
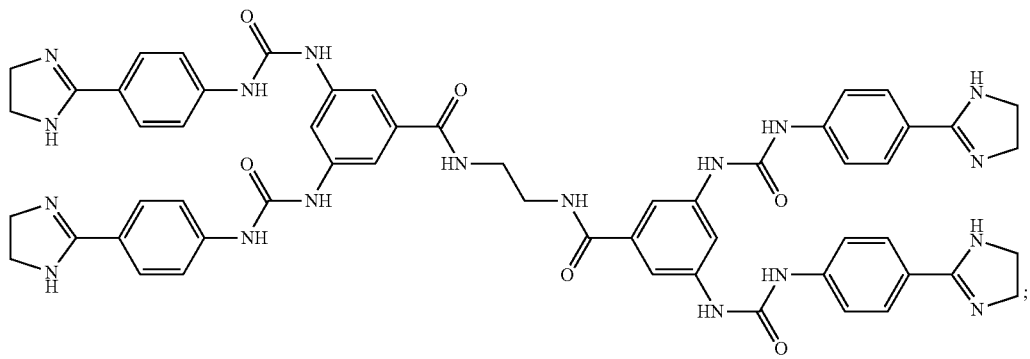
or a salt thereof.
In some embodiments, a compound that includes two moieties of Formula I, or Formula II, can be a compound of Formula III, for example, a compound having the structure:
(III.1)
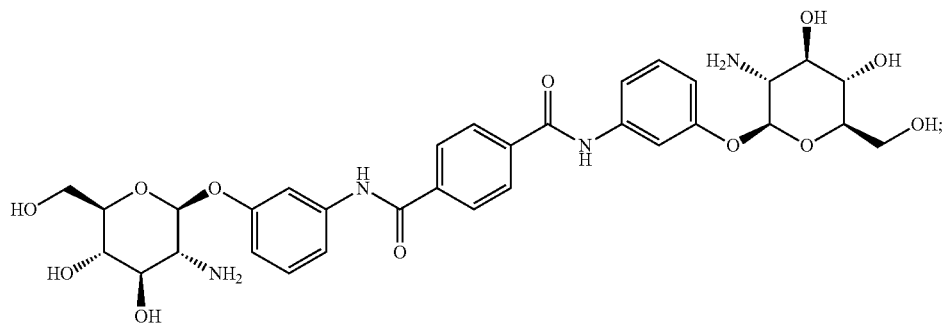
(III.2)
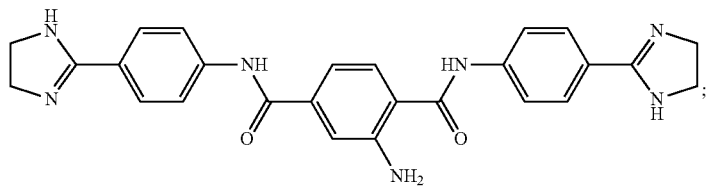

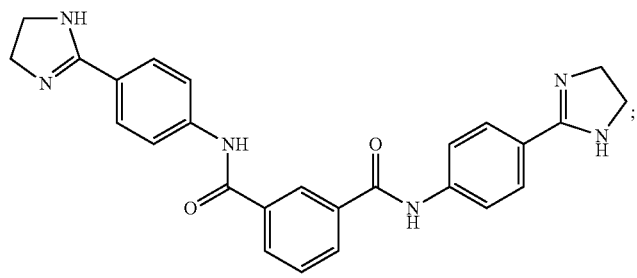
(III.3)
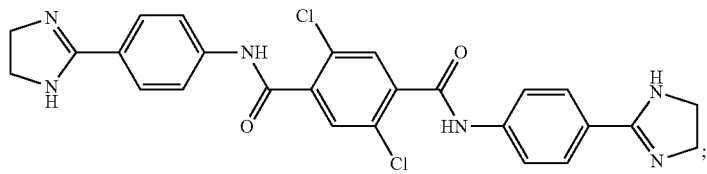
(III.4)
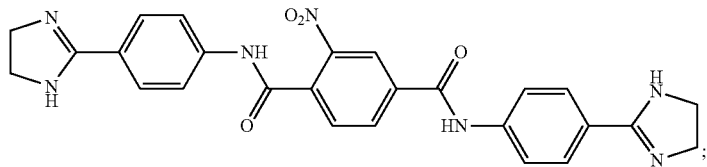
(III.5)
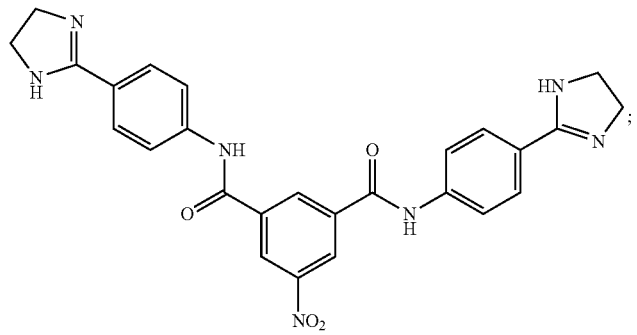
(III.6)
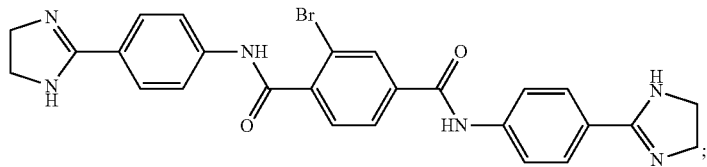
(III.7)
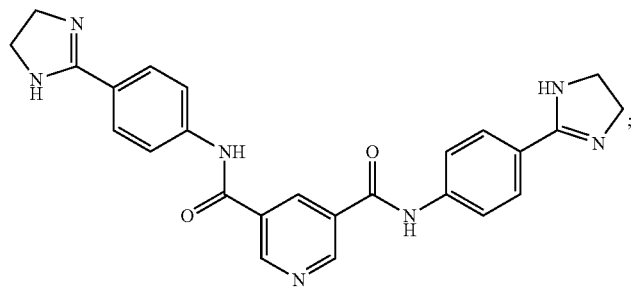
(III.8)

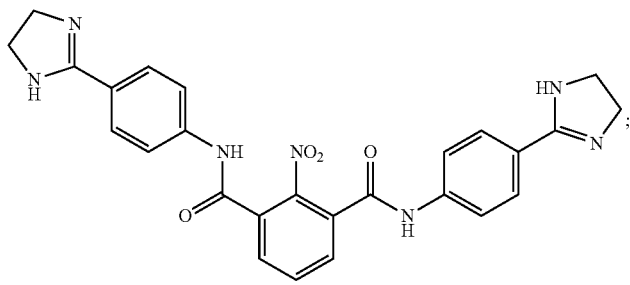
(III.9)
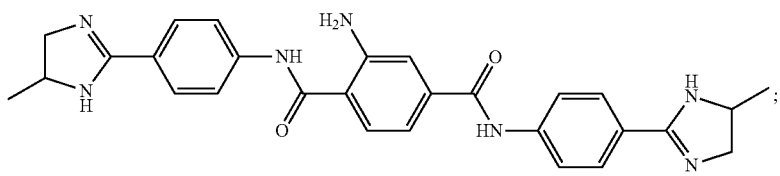
(III.10)
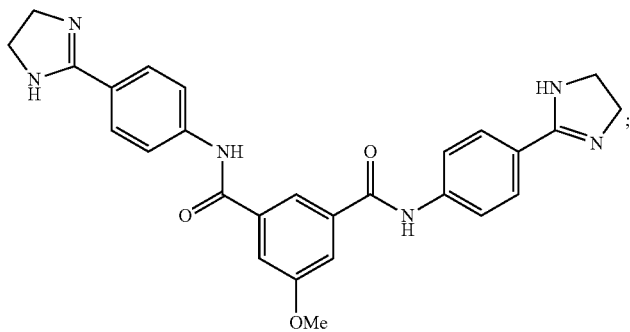
(III.11)
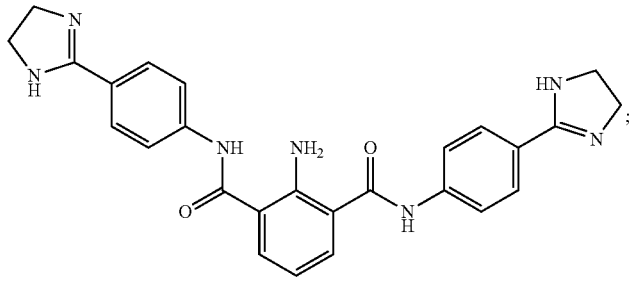
(III.12)
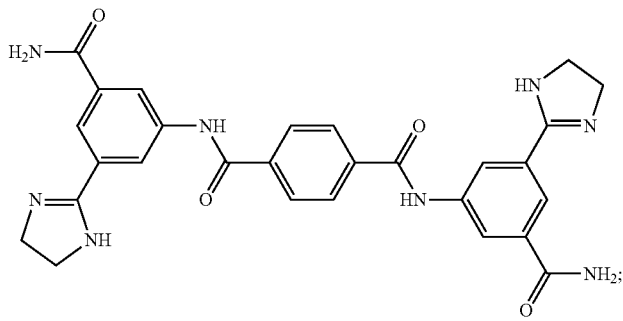
(III.13)

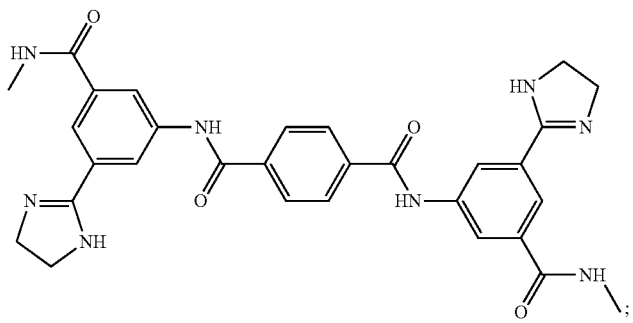
(III.14)
or a salt thereof.
In some embodiments, a compound that includes two moieties of Formula I, or Formula II, can be a compound of Formula IV, for example, a compound having the structure:
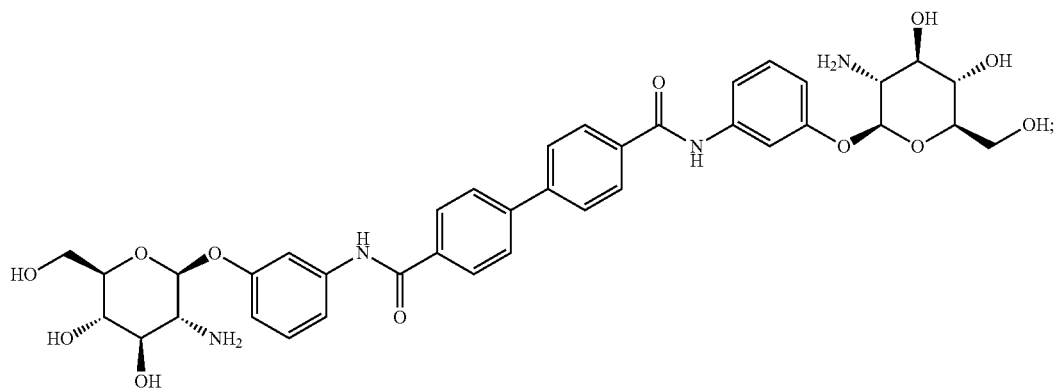
(IV.1)
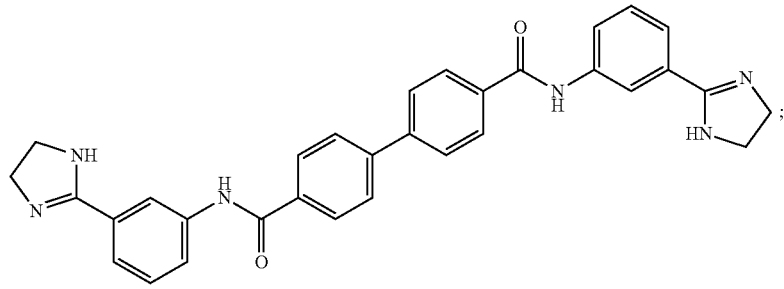
(IV.2)
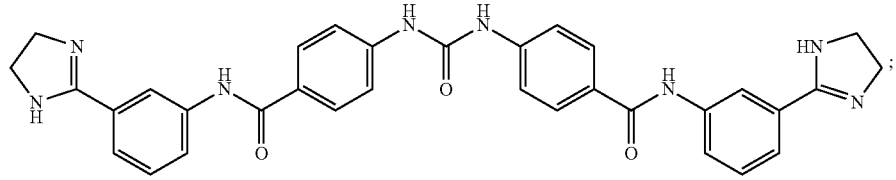
(IV.3)
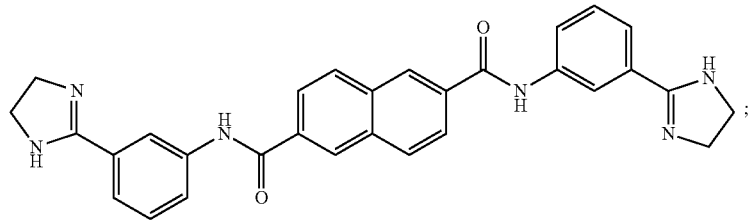
(IV.4)

or a salt or solvate thereof. A compound having Formula described above or a specific compound described or illustrated herein can be used to inhibit a prenyltransferase enzyme, such as UPPS or FPPS. The compounds can also kill or inhibit the growth of a bacterium, or a plurality of bacteria. Furthermore, the compounds described herein can restore the sensitivity of bacteria to other drugs such as methicillin, for example, when used in a drug combination therapy.

In one embodiment, a compound described herein can inhibit an isoprenoid biosynthesis enzyme when then compound is in contact with the enzyme, for example, in vitro or in vivo. The isoprenoid biosynthesis enzyme can be, for example, a prenyltransferase or other enzyme described herein. The $K_i$ of the compound can be, for example, less than about 30 µM less than about 20 µM less than about 10 µM less than about 5 µM less than about 2 µM, less than about 1.5 µM, less than about 1 µM, less than about 0.5 µM, less than about 400 nM, less than about 300 nM, less than about 250 nM, less than about 200 nM or less than about 150 nM.

The invention thus provides methods of inhibiting the activity of an enzyme such as an isoprenoid biosynthesis enzyme, for example, a prenyltransferase. The methods can include contacting the enzyme with a compound described herein, wherein the compound binds to the enzyme, thereby inhibiting the activity of the enzyme. The invention also provides methods of treating a bacterial infection in a mammal such as a human, wherein the bacterial infection is caused by a bacteria that has of an isoprenoid biosynthesis enzyme, wherein the method comprises administering to a mammal in need of such treatment an effective amount of a compound described herein, wherein the compound binds to the enzyme, thereby inhibiting the activity of the enzyme, thereby treating the bacterial infection or parasitic infection. The invention further provides methods of killing or inhibiting the growth of a bacterium wherein the bacteria has an isoprenoid biosynthesis enzyme. These methods can include contacting the bacterium with a compound described herein, wherein the compound binds to the enzyme of the bacterium, thereby killing or inhibiting the growth of the bacterium.

The invention also provides compounds that bind to DNA as well as UPPA and/or DPPS. These properties allow for use of the compounds to kill or inhibit the growth of bacteria, such as *Mycobacterium tuberculosis*, and therefore can be used to treat tuberculosis (noting that *M tuberculosis* uses decaprenyl diphosphate synthase (DPPS), not undecaprenyl diphosphate synthase (UPPS)). For example, compound 17 (BPH-1358) binds to DNA and UPPS, and inhibits *Mycobacterium tuberculosis* at a 0.4-0.5 µM concentrations. Compound BPH-1503 also inhibits *M. tuberculosis*, at 1 µM concentration. Based on our most recent data, potent UPPS inhibitors all bind to DNA as well as UPPS. Accordingly, the invention provides methods to bind DNA in combination with binding UPPS and/or DPPS, and therefore, can be used to treat tuberculosis.

General Synthetic Methods

Preparation of the compounds described herein can be prepared according to the methods in the Examples below, or may be prepared according to known techniques in the art of organic synthesis. Many alkynes, allenes, and linking groups are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Additional useful reactions well known to those of skill in the art are referenced in March's *Advanced Organic Chemistry Reactions, Mechanisms, and Structure*, 5$^{th}$ Ed. by Michael B. Smith and Jerry March, John Wiley & Sons, Publishers; and Wuts et al. (1999), *Protective Groups in Organic Synthesis*, 3$^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

Starting materials for the preparation of the compounds described herein are generally commercially available from chemical suppliers such as Sigma-Aldrich, Alfa-Aesar, or Acros Organics, or they can be prepared in a few steps from commercially available compounds. Preparation typically begins with a central linker such as an aryl or heteroaryl having carboxylic acids moieties for forming amides linkers. Hydroxymethyl moieties can be oxidized to carboxylic acids when the corresponding acids are not commercially available. Phenylalkynes can be prepared from haloaryl or haloheteroaryl starting materials using palladium catalysis or other known methods. Aryl or heteroaryl compounds with carboxylic acid substituents (the central linker moiety) can be conjugated to aryl or heteroaryl compounds having amine and nitrile substituents to form amide linkages (optionally in the presence of additional substituents). The nitrile groups of these intermediates can then be converted to amidines by condensation with the corresponding alkyldiamines. Specific methods and techniques are further described in the Examples section below and in the accompanying citations.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet.

Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

All reagents utilized were purchased from Aldrich (Milwaukee, Wis.) or Alfa Aesar (Ward Hill, Mass.). NMR spectra were obtained on 400 MHz ($^1$H) or 500 MHz Varian (Palo Alto, Calif.) Unity spectrometers. Compounds 10, 14, 15 were available from previous work (Durrant et al., *Chem Biol Drug Des* 2011, 78(3):323-332; Zhang et al., *ACS Med Chem Lett* 2012, 3(5):402-406). The syntheses of 11, 12, 13, 16, 17, and 18 are described below.

The following abbreviations are defined as follows: UPP, undecaprenyl diphosphate; UPPS, UPP synthase; FPP, farnesyl diphosphate; FPPS, FPP synthase; FSPP, S-thiolo-FPP; IPP, isopentenyl diphosphate; DMAPP, dimethylallyl diphosphate; ROC/AUC, receiver operating characteristic/area under the curve.

Example 1

Preparation of Enzyme-Inhibiting Compounds (Dodecyloxy)-6-hydroxybenzoic acid (11). To a mixture of 5-hydroxy-2, 2-dimethyl-4H-benzo[d][1,3]dioxin-4-one (1 g, 5.2 mmol) and 1-dodecanol (1.6 g, 7.5 mmol) in THF (20 mL) at 0° C. were added triphenylphosphine (2.0 g, 7.5 mmol) and DIAD (1.5 mL, 7.5 mmol). The mixture was then stirred overnight at room temperature. The reaction mixture was concentrated and purified by column chromatography (ethyl acetate/hexane 1:8). Saponification with 4M NaOH (5 equiv) under reflux and acidification with 1M HCl afforded 11 as a white solid (1.07 g, 70%). $^1$H NMR (CDCl$_3$, 500 MHz) δ: 7.36 (t, J=8.5 Hz, 1 H), 6.68 (d, J=8.5 Hz, 1 H), 6.45 (d, J=8.5 Hz, 1 H), 4.20 (t, J=6.5 Hz, 2 H), 1.91-1.87 (m, 2 H), 1.47-1.43 (m, 2 H), 1.28-1.24 (m, 16 H), 0.86 (t, J=6.5 Hz, 3 H) ppm. $^{13}$C NMR (CDCl$_3$, 125 MHz) δ: 171.2, 164.5, 158.3, 135.8, 130.3, 112.4, 102.4, 71.0, 32.1, 29.8, 29.7, 29.7, 29.6, 29.5, 29.40, 29.1, 26.1, 22.9, 14.4. HRMS (ESI): m/z [M+H]$^+$ calcd. for C$_{19}$H$_{31}$O$_4$ 323.2222; found 323.2231.

2-(3-(Decyloxy)benzamido)-5-nitrobenzoic acid (12). To a mixture of 3-(decyloxy)benzoyl chloride (296 mg, 1 mmol) and 2-amino-5-nitrobenzoic acid (182 mg, 1 mmol) in CH$_2$Cl$_2$ (20 mL) was added Et$_3$N (1 mL). The mixture was stirred overnight and washed with water (5 mL) and 1M HCl (4 mL) and then concentrated. Recrystallization from ethyl acetate/hexane 1:1 afforded 12 as white powder (185 mg, 42%). $^1$H NMR (CDCl$_3$, 500 MHz) δ: 12.17 (s, 1 H), 9.16 (d, J=9.5 Hz, 1 H), 9.03 (d, J=3.0 Hz, 1 H), 8.47 (dd, J=9.5, 3.0 Hz, 1 H), 7.54 (d, J=1.0 Hz, 1 H), 7.53 (d, J=8.0 Hz, 1 H), 7.42 (t, J=8.0 Hz, 1 H), 7.13 (dd, J=8.0, 1.0 Hz, 1 H), 4.03 (t,J=6.5 Hz, 2 H), 1.82-1.78 (m, 2 H), 1.47-1.43 (m, 2 H), 1.26-1.22 (m, 12 H), 0.86 (t, J=7.0 Hz, 3 H). $^{13}$C NMR (CDCl$_3$, 125 MHz) δ: 169.6, 160.0, 147.6, 142.1, 135.3, 130.5, 130.3, 128.0, 121.0, 120.1, 119.3, 114.2, 113.6, 68.6, 32.1, 29.80, 29.8, 29.6, 29.5, 29.4, 26.6, 22.9, 14.3. HRMS (ESI): m/z [M+H]$^+$ calcd. for C$_{24}$H$_{31}$N$_2$O$_6$ 443.2182; found 443.2174.

(5-bromo-2-((3-(octyloxy)benzyl)oxy)phenyl)phosphonic acid (13). To a mixture of diethyl (5-bromo-2-hydroxyphenyl)phosphonate (1.54 g, 5.0 mmol) and 3-octyloxybenzyl alcohol (1.2 g, 5.0 mmol) in THF (20 mL) at 0° C. were added triphenylphosphine (2.0 g, 7.5 mmol) and DIAD (1.5 mL, 7.5 mmol). The mixture was then stirred overnight at room temperature. The reaction mixture was concentrated and purified by column chromatography (ethyl acetate/hexane 1:1). The diethyl ester of 13 was then treated with 8 equivalent of TMSBr in anhydrous CH$_2$Cl$_{12}$ (15 mL) overnight. After removal of the solvent, the concentrated oil was treated with 10 mL methanol to afford 13 as white solid (1.62 g, 68%, two steps). $^1$H NMR (DMSO-D$_6$, 400 MHz) δ: 7.70 (dd,J=14.8, 2.8 Hz, 1 H), 7.54 (dd,J=8.8, 2.8 Hz, 1 H), 7.20 (t, J=7.6 Hz, 1 H), 7.10 (s, 1 H), 6.99 (m, 1 H), 6.98 (m, 1 H), 6.77 (dd, J=2.4, 8.0 Hz, 1 H), 5.16 (s, 2 H), 4.13 (t, J=6.8 Hz, 2 H), 1.64-1.60 (m, 2 H), 1.36-1.32 (m, 2 H), 1.25-1.21 (m, 8 H), 0.81 (t, J=6.8 Hz, 3 H) ppm. $^{13}$C NMR (DMSO-D$_6$, 125 MHz) δ: 171.4, 159.4, 159.1, 139.0, 136.2, 130.1, 126.0, 124.6, 119.5, 115.9, 114.6, 113.3, 69.7, 60.6, 31.9, 31.3, 29.4, 29.3, 26.15, 22.7, 14.6. HRMS (ESI): m/z [M+H]$^+$ calcd. for C$_{21}$H$_{29}$BrO$_5$P 471.0936; found 471.0940.

N$^1$, N$^4$-bis(3-(4,5-dihydro-1H-imidazol-2-yl)phenyl)-2-nitroterephthalamide (16). Compound 16 was obtained from the NCI screening library and its identity was confirmed by $^1$H NMR, $^{13}$C NMR and HRMS. $^1$H NMR (DMSO-D$_6$, 500 MHz) δ: 8.72 (s, 1 H), 8.44 (d, J=7.5 Hz, 1 H), 7.99 (d,J=7.5 Hz, 1 H), 7.90-7.81 (m, 6 H), 7.71 (d,J=8.5 Hz, 2 H), 3.60 (s, 8 H). $^{13}$C NMR (DMSO-D$_6$, 125 MHz) δ: 163.8, 163.5, 147.0, 141.0, 137.5, 135.0, 133.9, 130.5, 128.6, 128.4, 126.9, 124.2, 120.5, 119.7, 39.8. HRMS (ESI): m/z [M+H]$^+$ calcd for C$_{26}$H$_{24}$N$_7$O$_4$, 498.1890; found 498.1882.

N$^4$, N$^{4'}$-bis(3-(4,5-dihydro-1H-imidazol-2-yl)phenyl)-[1,1'-biphenyl]-4,4'-dicarboxamide (17) (BPH-1358). To a mixture of 4,4'-diphenyl dicarbonyl chloride (1.39 g, 5 mmol), 3-aminobenzonitrile (1.18 g, 10 mmol) in anhydrous THF (20 mL) was added Et$_3$N (2.1 mL, 15 mmol) and the mixture was stirred at room temperature overnight. After filtration, the white solid was washed with water (20 mL) and ethyl acetate (10 mL) and then dried. Sodium hydrosulfide hydrate (100 mg), ethylenediamine (2 mL) and dimethylacetamide (10 mL) were then added and stirred overnight at 140° C. Upon removal of the solvent, the solid was washed thoroughly with water and then ethyl acetate (10 mL). To the suspension of the crude product in 10 mL of water were added two equivalents of methyl sulfonic acid. Removal of water afforded 17 as its methanesulfonic acid salt (1.44 g, 40%). $^1$H NMR (DMSO-D$_6$, 500 MHz) δ: 10.68 (s, 2 H), 10.52 (s, 4 H), 8.50 (s, 2 H), 8.12 (d, J=9.0 Hz, 4 H), 8.02-7.98 (m, 2 H), 7.96 (d, J=9 Hz, 4 H), 7.68-7.58 (m, 4 H), 4.00 (s, 8 H), 2.36 (s, 6 H). $^{13}$C NMR (DMSO-D$_6$, 125 MHz) δ: 166.1, 166.1, 143.0, 140.6, 134.4, 130.6, 129.2, 127.7, 127.0, 124.3, 123.5, 120.8, 45.3. HRMS (ESI): m/z [M+H]$^+$ calcd. for C$_{32}$H$_{29}$N$_6$O$_2$ 529.2361, found 529.2352.

2,2'-((1,3-phenylenebis(ethyne-2,1-diyl))bis(3-bromo-5,1-phenylene))diethanamine (18). Compound 18 was synthesized as reported (Yang et al., *Proc Natl Acad Sci USA* 2008, 105(52):20595-20600). $^1$H NMR (DMSO-D$_6$, 500 MHz) δ: 7.66-7.42 (m, 10 H), 3.19 (t, J=8.0 Hz, 4 H), 2.95 (t, J=8.0 Hz, 4 H) ppm. $^{13}$C NMR (DMSO-D$_6$, 125 MHz) δ: 158.8, 141.2, 135.6, 133.6, 133.2, 132.8, 131.7, 130.4, 124.9, 123.3, 122.6, 89.7, 40.8, 32.9. HRMS (ESI): m/z [M+H]$^+$ calcd for C$_{26}$H$_{23}$Br$_2$N$_2$, 521.0228; found 521.0214.

Example 2

Antibacterial Drug Leads Targeting Isoprenoid Biosynthesis

In previous work, we and others reported the discovery of several UPPS inhibitors including bisphosphonates such as BPH-629 (5) (Guo et al., *Proc Natl Acad Sci USA* 2007, 104(24):10022-10027), tetramic acids such as 6 (Peukert et al., *Bioorg Med Chem Lett* 2008, 18(6):1840-1844), as well as diketoacids such as 7 (Zhang et al., *ACS Med Chem Lett* 2012, 3(5):402-406), and benzoic acids such as 8 (Durrant et al., *Chem Biol Drug Des* 2011, 78(3):323-332); FIG. 2.

Figure 4:
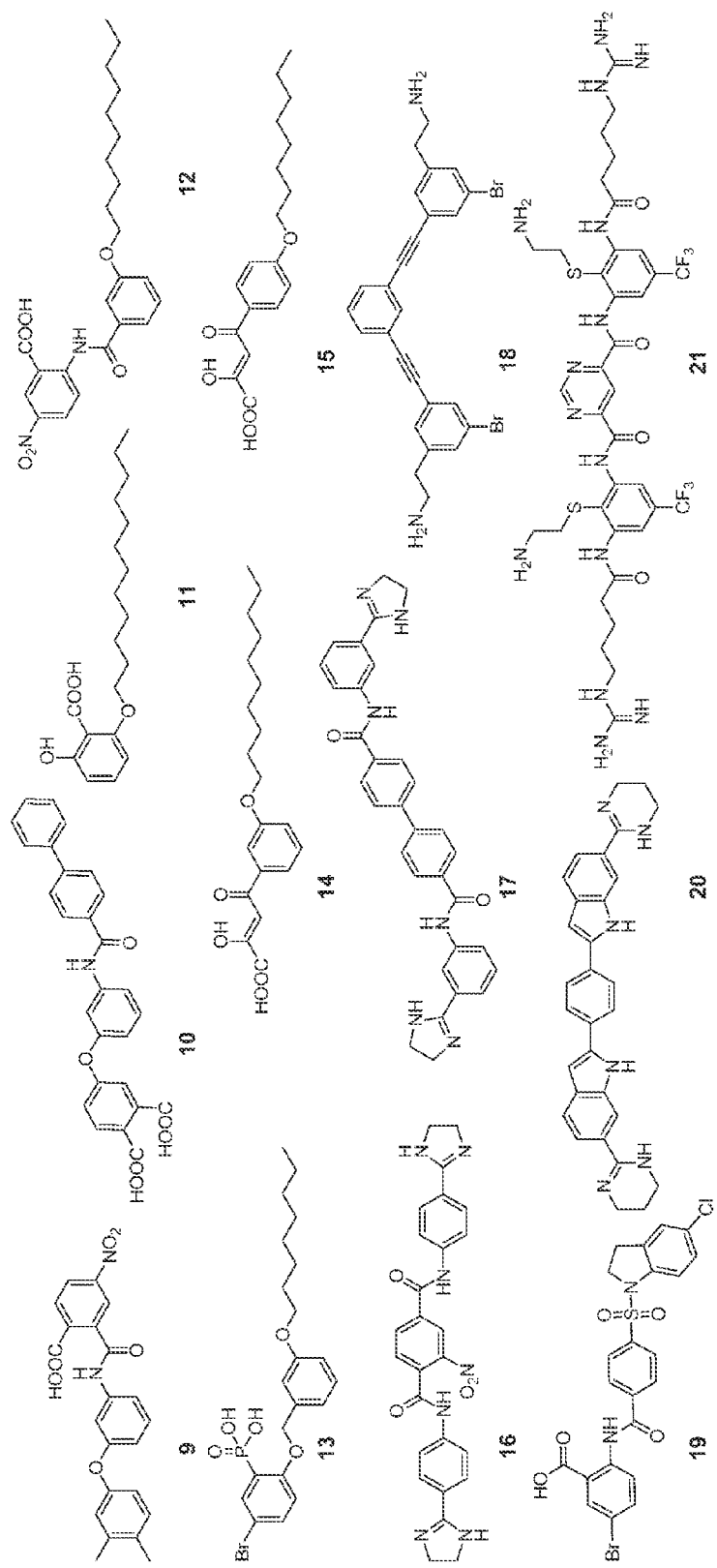
FIG. 4. Chemical structures of certain new UPPS inhibitors and drug candidates.

New UPPS inhibitors. Based on in silico high throughput screening and hit development (FIG. 3) we produced a small series of benzoic (9-12), phosphonic (13) and diketo acids (14, 15) that had activity against UPPS (FIG. 4). In addition to these anionic species, we discovered several potent cationic inhibitors (16-18). This was unexpected from both a computational and experimental standpoint since these compounds do not mimic the (anionic) FPP substrate, and the UPPS mechanism is not thought to involve carbocation intermediates. We thus sought to determine how these inhibitors bind to their UPPS target, by obtaining crystal structures of 8-16 and 18 bound to *E. coli* UPPS.

Figure 5:
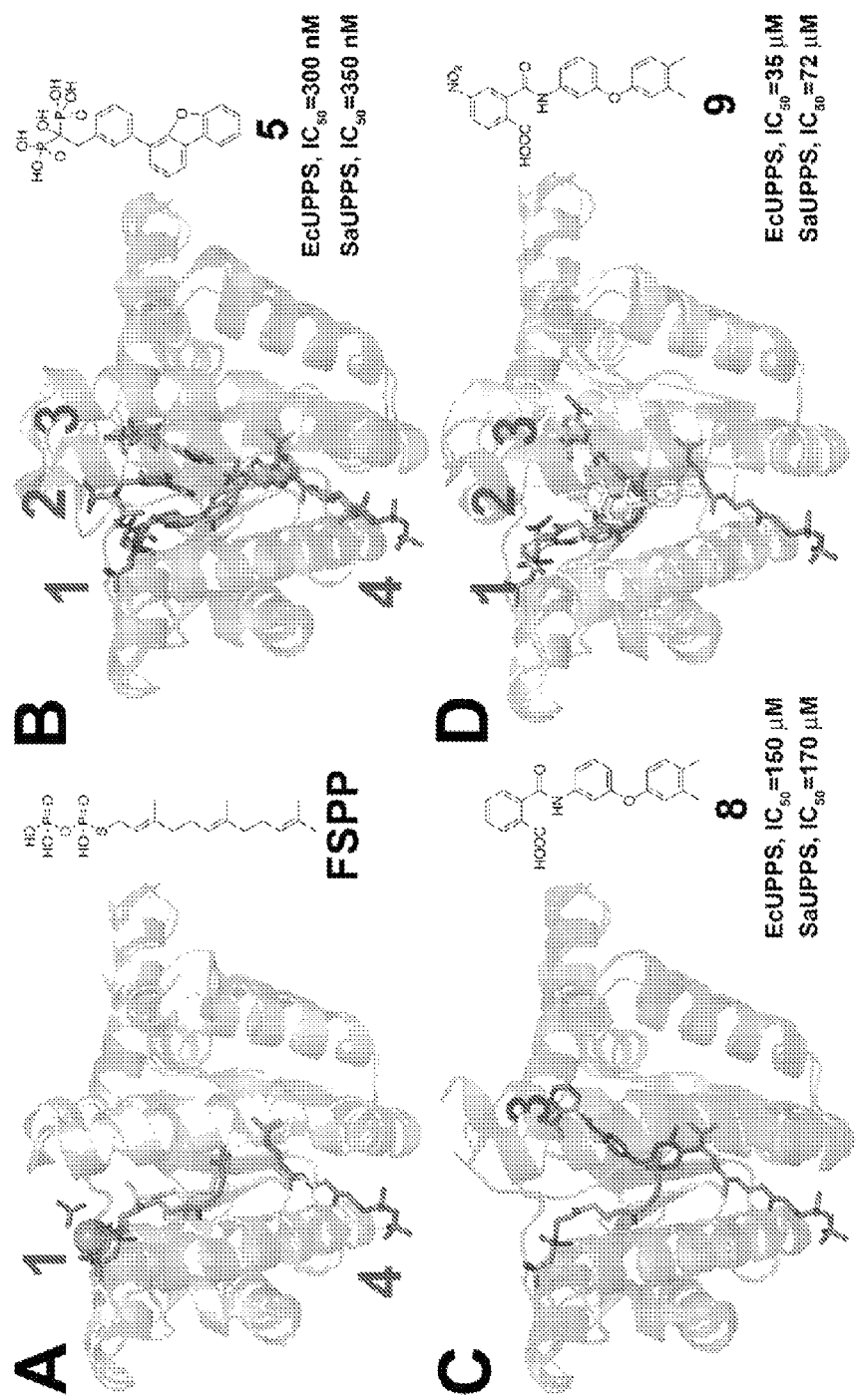
FIG. 5. X-ray structures of *E. coli* UPPS showing substrate and inhibitor-binding sites. (A) FSPP binds to site-1 (PDB ID code 1X06) and FPP binds to sites 1, 4 (PDB ID code 1V7U). (B) A bisphosphonate (5) binds to sites 1-4 (PDB ID code 2E98). (C) Benzoic acid inhibitor 8 binds to site-3 (PDB ID code 3SGT), superimposed on FPP-bound structure (PDB ID code 1V7U). (D) Benzoic acid inhibitor 9 binds to sites 1-3 (PDB ID code 3SGV), superimposed on FPP-bound structure (PDB ID code 1V7U). The large numbers indicate sites 1-4. See also Zhu et al., *Proc Natl Acad Sci USA* 2013, 110(1):123-128.

The four inhibitor binding sites in UPPS. UPPS functions by sequentially adding IPP to an allylic substrate, initially FPP. It might reasonably be expected, then, that anionic inhibitors with lipophilic side-chains would bind to the FPP substrate site, as shown in FIG. 5A (back molecule; PDB ID code 1X06). However, in a second structure (PDB ID code 1V7U) two FPP molecules bind, one in the substrate site and the other in a second site at the "bottom" of the protein (FIG. 5A, front molecule). Moreover, with the bisphosphonate inhibitor 5, there are actually four binding sites (sites 1-4) that can be occupied, FIG. 5B (PDB ID code 2E98) in which the side chains in each of the four inhibitor molecules occupy the large hydrophobic center of the protein that normally accommodates the $C_{55}$ side chain in the UPP product. With the two less-active benzoic acid inhibitors, 8 and 9, we find that only site-3 (FIG. 5C; PDB ID code 3SGT) or sites 1, 2 and 3 are occupied (FIG. 5D; PDB ID code 3SGV)—but the activity of both of these inhibitors is weak (8, *E. coli* UPPS, $IC_{50}$=150 µM; *S. aureus* UPPS, 170 µM; 9, *E. coli* UPPS, $IC_{50}$=35 µM; *S. aureus* UPPS, 72 µM; Table 1). Full data acquisition and structure refinement details are in Table 2 (see FIG. 6). So, with these two benzoic acid inhibitors, binding to sites 1, 2 or 3 correlates only to weak UPPS inhibition.

TABLE 1

Enzyme and cell growth inhibition results.

| ID | *E. coli* UPPS $IC_{50}$ (µM) | *S. aureus* UPPS $IC_{50}$ (µM) | *E. coli* $MIC_{90}$ (µg/mL) | *S. aureus* $MIC_{90}$ (µg/mL) |
|---|---|---|---|---|
| 5 | 0.28 | 0.35 | >32 | >32 |
| 7 | 0.56 | 0.75 | >32 | >32 |
| 8 | 150 | 170 | >32 | N.D. |
| 9 | 35 | 72 | >32 | N.D. |
| 10 | 3.2 | 6.9 | 16 | N.D. |
| 11 | 2.2 | 1.7 | >32 | N.D. |
| 12 | 3.0 | 0.49 | >32 | >32 |
| 13 | 0.92 | 2.5 | >32 | 32 |
| 14 | 1.9 | 0.73 | >32 | 0.5 |
| 15 | 0.51 | 2.0 | >32 | 0.25 |
| 16 | 4.8 | 4.9 | 8 | >32 |
| 17 | 0.11 | 0.11 | 4 | 0.25 |
| 18 | 6.1 | 1.4 | 8 | >32 |
| 19 | 1.4 | 1.6 | >32 | 1 |

Figure 7:
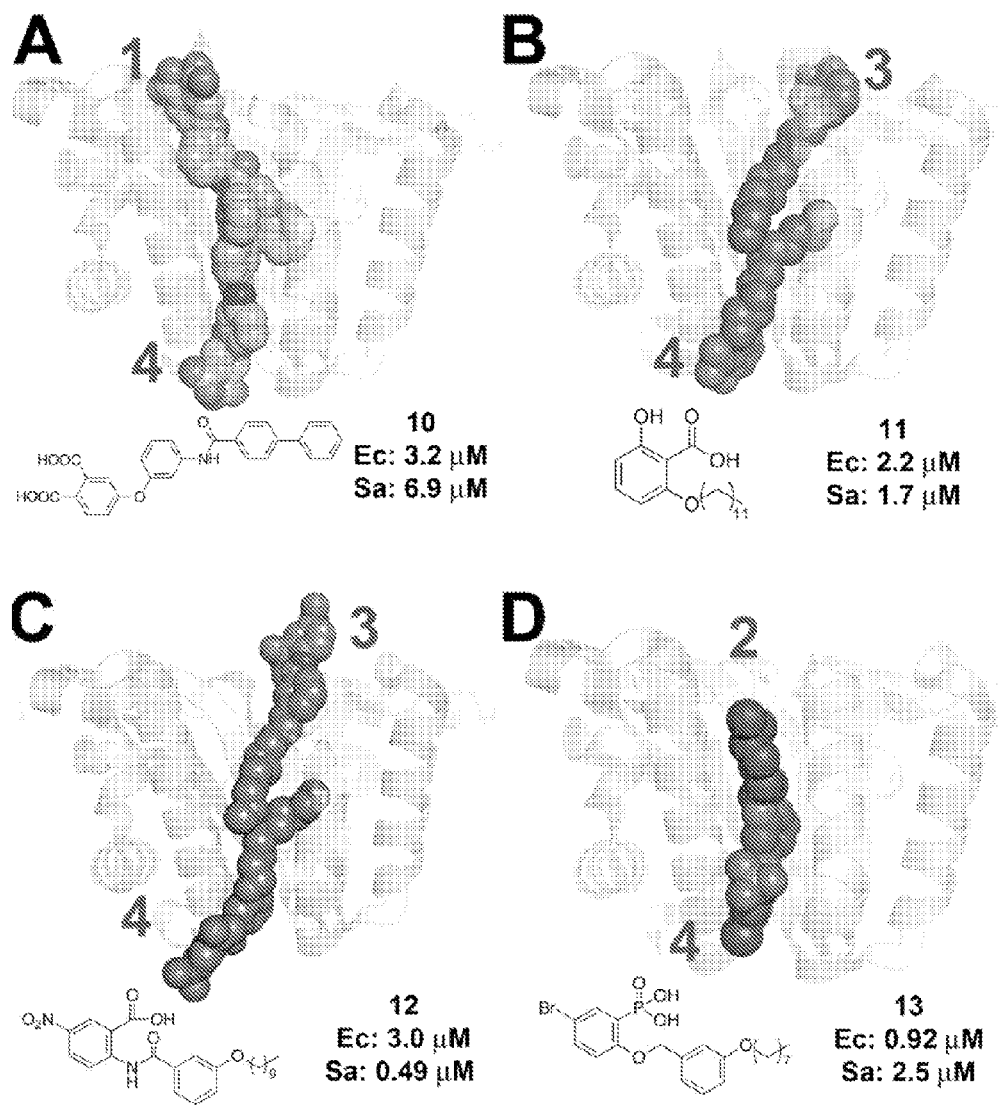
FIG. 7. Crystal structures of the more potent benzoic acids and a phosphonate inhibitors. (A) 10 (PDB ID code 3SGX). (B) 11 (PDB ID code 3HS0). (C) 12 (PDB ID code 4H2O). (D) 13 (PDB ID code 4H38). In each case site 4 is occupied, together with either site 1, 2 or 3, indicating the importance of site 4 binding for good activity.
Figure 8:
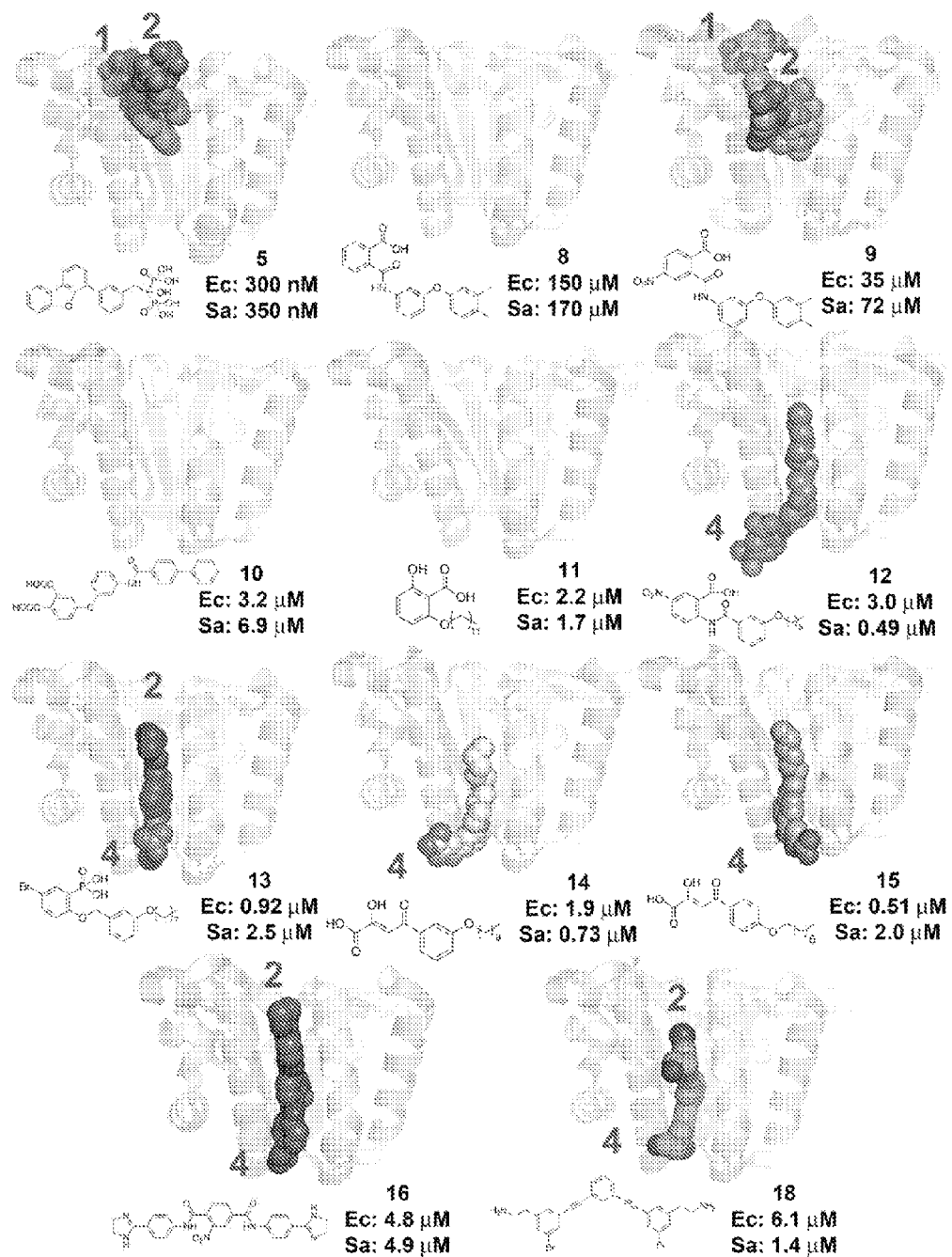
FIG. 8. Structures of inhibitors bound to *E. coli* UPPS.

Potent benzoic acid inhibitors bind to site-4. We next determined the structures of the three potent benzoic acid inhibitors (10-12, FIG. 4) bound to UPPS (FIG. 7A-C). Each of these molecules contains a long hydrophobic side-chain and, on average, the $IC_{50}$ values against both *E. coli* and *S. aureus* UPPS are ~3 µM, Table 1. What is notable about these x-ray structures is that in each case, site-4 is occupied, together with either sites 1, 2 or 3. Full data acquisition and structure refinement details are in Table 2. In addition, we found that the aryl phosphonate inhibitor 13 also occupied two sites, FIG. 7D. However, there are two chains in one asymmetric unit and site-occupancies in the two chains are variable: the lower site-occupancy chains are shown in FIG. 8. These four structures suggest that good UPPS inhibition correlates with occupancy of site-4.

Diketoacids, a bisamidine and a bisamine also target site-4. In our previous work (Zhang et al., *ACS Med Chem Lett* 2012, 3(5):402-406), we found that the diketoacid 15 had potent cell growth inhibition activity with the following $MIC_{90}$ values: 0.25-0.5 µg/mL against *S. aureus*, 0.5 µg/mL against *Bacillus anthracis*, 4 µg/mL against *Listeria monocytogenes* and *Enterococcus faecium*, and 1 µg/mL against *Streptococcus pyogenes*, but little toxicity toward human cell lines (>20 µM). We therefore next determined the structure of 15 and a second diketoacid (14), bound to UPPS. As can be seen in FIG. 9A and B, both diketoacids bind to site-4, with 14 also binding to site-3. The observation that 15 binds only to site-4 is of interest since this inhibitor has very good antibiotic activity. Additionally, the occupation of site-4 in both structures is consistent with the results for the other potent anionic inhibitors; FIG. 7.

A surprising result from the in silico screening work (FIG. 3) was that bisamidines such as 16 had modest activity against UPPS. Moreover, the biphenyl bisamidine 17 showed potent activity against UPPS ($IC_{50}$ value of 0.1 µM) as well as a $MIC_{90}$ of 0.25 µg/mL against *S. aureus* (USA300, MRSA strain). We also found that another dicationic species 18 was a UPPS inhibitor active against *S. aureus* (Table 1). We were unable to obtain the structure of 17 bound to UPPS, but we did obtain structures of 16 and 18 bound to UPPS.

Figure 9:
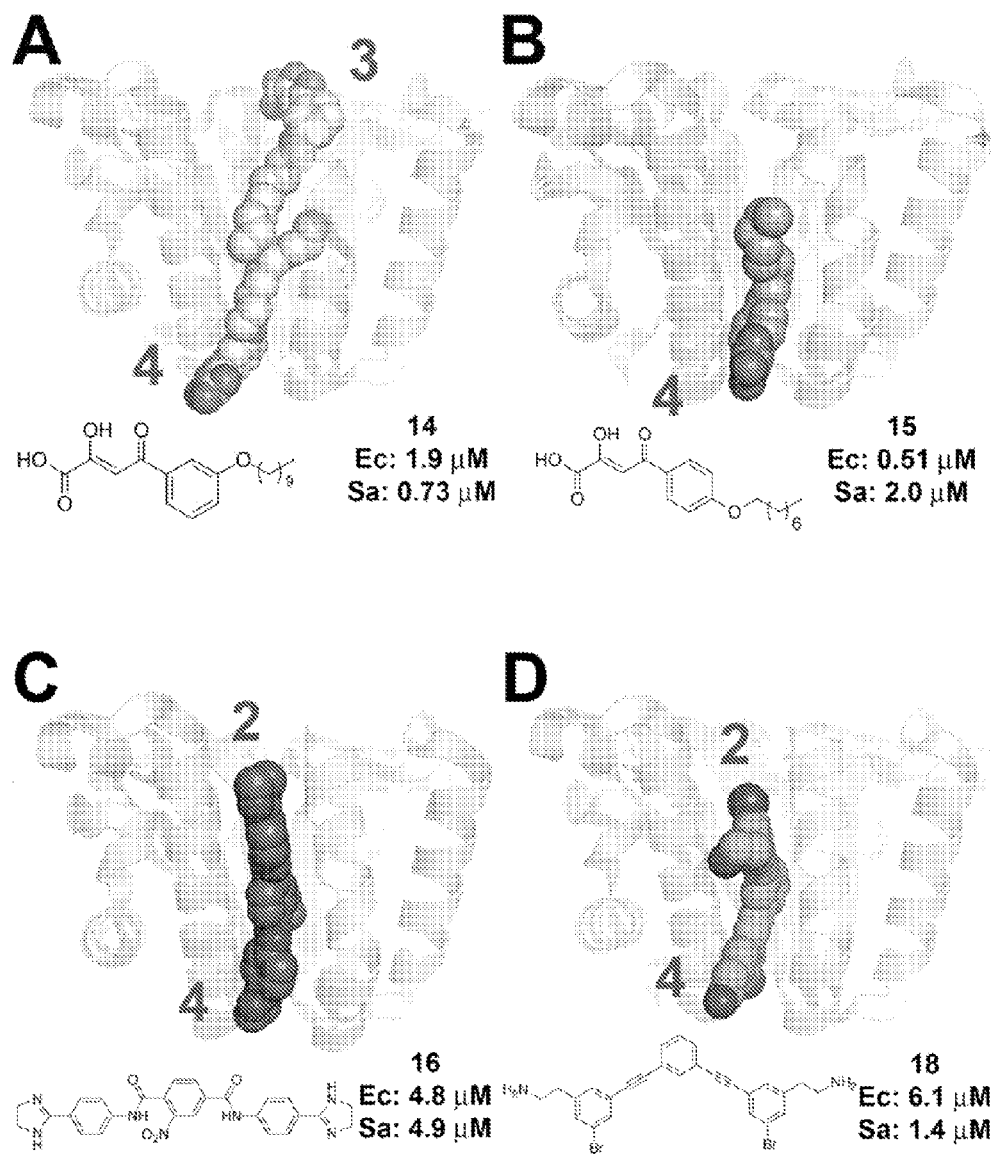
FIG. 9. Crystal structures of diketo acids and two dicationic inhibitors bound to *E. coli* UPPS. (A) 14 (PDB ID code 4H3C). (B) 15 (PDB ID code 4H3A). (C) 16 (PDB ID code 4H2J). (D) 18 (PDB ID code 4H2M). The common feature in each case is binding to site 4.
Figure 10:
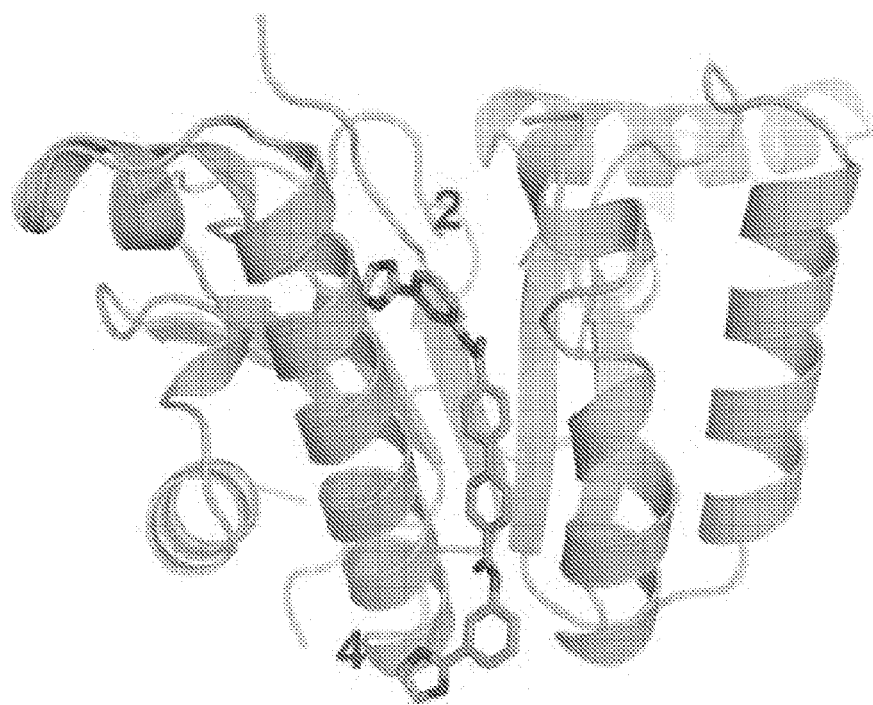
FIG. 10. Glide XP docking result for 17 bound to *E. coli* UPPS showing binding to sites 2 and 4.

With these two cationic inhibitors, rather than two individual molecules binding, we observe that a single molecule binds, with its polar, cationic groups located at or near the protein's surface, while the hydrophobic "spacer" is buried inside the protein's hydrophobic interior, FIG. 9 and D (PDB ID codes 4H2J, 4H2M). While we did not initially succeed in crystallizing the most potent lead 17, a similar "polar-hydrophobic-polar" binding arrangement in which the biphenyl group is buried seems very likely for this species also, and is supported by the results of computational docking, as shown in FIG. 10.

Figure 11:
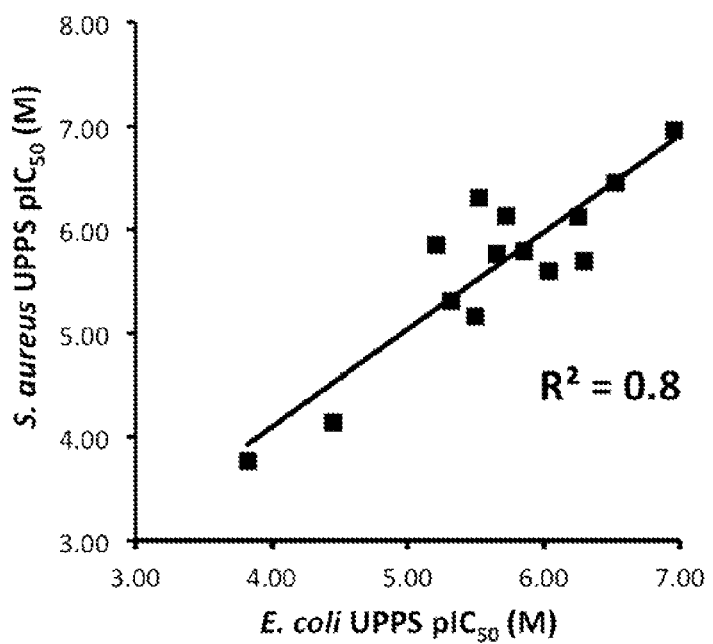
FIG. 11. Correlation between *E. coli* and *S. aureus* UPPS inhibition by the compounds listed in Table 1.

Comparison of *E. coli* and *S. aureus* UPPS structures, and their inhibition. In this work, we determined the activity of each inhibitor against both *E. coli* UPPS and *S. aureus* UPPS, finding that there is a very good correlation ($R^2$=0.8) between the 14 sets of $pIC_{50}$ (=$-\log_{10}IC_{50}$) values (Table 1; FIG. 11). This is notable because 18 of the top 20 residues in a SCORECONS analysis (Valdar, Scoring residue conservation. *Proteins* 2002, 48(2):227-241) of *E. coli* UPPS are present in *S. aureus* UPPS, and most other bacterial UPPSs (Table 3A). We were not able to determine the x-ray structures of any inhibitor bound to *S. aureus* UPPS, but we did determine the structure of the protein with a bound FPP (PDB ID code 4H8E; full data acquisition and structure refinement details are in Table 3B).

TABLE 3A

SCORECONS using *E. coli* UPPS as a target. Asp26 is the most essential residue and binds to $Mg^{2+}$ in the active site.

| Ranking | Residue No. | SCORECONS Score** | Residue | Alignment |
|---|---|---|---|---|
| 1 | 26 | 0.988 | D | DDDDDDDDDDDDDDDDDDDDDDDDDDDDDDDDD |
| 2 | 30 | 0.984 | R | RRRRRRRRRRRRRRRRRRRRRRRRRRRRRRRRR |
| 3 | 28 | 0.976 | N | NNNNNNNNNNNNNNNNNNNNNNNNNNNNNNNNN |
| 4 | 74 | 0.968 | N | NNNNNNNNNNNNNNNNNNNNNNNNNNNNNNNNN |
| 5 | 20 | 0.964 | H | HHHHHHHHHHHHHHHHHHHHHHHHHHHHHHHHH |
| 6* | 190 | 0.960 | D | DDDDDDDEDDDDEDDDDEDDDDDDDEDDDDDDDD |
| 7 | 77 | 0.953 | R | RRRRRRRRRRRRRRRRRRRRRRRRRRRRRRRRR |
| 8 | 204 | 0.945 | F | FFFFFFFFFFFFFFFFFFYFFFFFFFFFFFFFFFFFFFFFFFY |
| 9 | 145 | 0.941 | Y | YYYYYYYYYYYYYYYYYYYYYYYYYYYYYYYYYYYYYYYYY |
| 10 | 194 | 0.937 | R | RRRRRRRRRRRRRRRRRRRRRRRRRRRRRRRRR |
| 11 | 200 | 0.933 | R | RRRRRRRRRRRRRRRRRRRRRRRRRRRRRRRRR |
| 12 | 202 | 0.925 | S | SSSSSSSSSSSSSSSSSSSSSSSSSSSSSSSSS |
| 13* | 18 | 0.921 | C | CPPPPPPPPPPPPPPPPPPPPPPPPPPPPPPPP |
| 14 | 71 | 0.917 | S | SSSSSSSSSSSSSSSSSSSSSSSSSSSSSSSSS |
| 15 | 32 | 0.905 | A | AAAAAAAAAAAAAAAAAAAAAAAAAGAAAAAAA |
| 16 | 207 | 0.901 | W | WWWWWWWWWWWWWWWWWWWWWWWWW |
| 17 | 221 | 0.897 | W | WWWWWWWWWWWWWWWWWWWWWWWWW |
| 18 | 81 | 0.889 | E | EEEEEEEEEEEEEEEEEEEEEEEEEEEEEEEEE |
| 19 | 43 | 0.881 | H | HHHHHHHHHHHHHHHHHHHHHHHHHHHHH |
| 20 | 66 | 0.874 | T | TTTTTTTTTTTTTTTTTTTTTTTTTTSTTTTTTT |

*Residues are different in *E. coli* UPPS and *S. aureus* UPPS.
**Valdar, Scoring residue conservation. *Proteins* 2002, 48(2): 227-241.

TABLE 3B

Data collection and refinement statistics for *S. aureus* UPPS.

| Crystals | SaUPPS/FPP (4H8E) |
|---|---|
| *Data collection* | |
| Space group | $P4_12_12$ |
| Unit cell dimension a, b, c (Å) | 57.303, 57.303, 158.824 |
| X-ray source | APS 21-ID-G |
| Wavelength (Å) | 0.97857 |
| Resolution (Å)* | 50.00-1.30 (1.32-1.30) |
| # of reflection | 916,358 |
| Unique | 66,126 (3,237) |
| Completeness (%) | 100.0 (100.0) |
| R-merge | 0.077 (0.400) |
| I/σ(I) | 33.9 |
| Multiplicity | 13.9 (11.3) |
| *Refinement statistics* | |
| Resolution range (Å) | 32.64-1.30 |
| R-work/R-free (%) | 17.4/19.4 |
| RMSD | |
| Bond lengths | 0.032 |
| Bond angles | 2.655 |
| No. of atoms | |
| Protein | 1,918 |
| Ligand | 30 |
| B average (Å$^2$): | 13.11 |
| B average (Å$^2$): | 11.70 |

*Values in the parentheses are for the highest resolution shells.

Figure 12:
FIG. 12. Superimposition of *E. coli* UPPS structure (PDB ID code 1X06) and *S. aureus* UPPS structure (PDB ID code 4H8E). The Cα root-mean square deviation is 0.91 Å over 202 residues. See also Zhu et al., *Proc Natl Acad Sci USA* 2013, 110(1):123-128.

*S. aureus* co-crystallized with FPP in site-1 together with a $SO_4^{2-}$ in the IPP binding sites, as reported in U.S. Patent Publication No. 2005/0208639 (Ammirati and Pandit). A superposition of the *S. aureus* and *E. coli* proteins is shown in FIG. 12 where we find a Cα root-mean square deviation of 0.91 Å over 202 residues, indicating that both structures are very similar (in the presence of FPP/FSPP and either IPP or $SO_4^{2-}$), consistent with the $pIC_{50}$ correlation.

Relationship to other inhibitors: UPPS a missing link. The structures of several of the UPPS inhibitors described here are similar to (and with 18, the same as) those being developed as anti-infective drug leads but whose mechanisms of action are not clear. For example, the chemical structures of the benzoic acid inhibitors are similar to those of anthranilic (ortho-aminobenzoic) acids reported by Larsen et al. and Mott et al. having activity against *S. aureus* (Larsen et al., *Bioorg Med Chem Lett* 2006, 16(24):6173-6177; and Mott et al., *J Antimicrob Chemother* 2008, 62(4): 720-729, respectively). The molecular mechanism of action of these inhibitors was initially thought to involve inhibition of translation/termination, but in later work this inhibition was not found to correlate with cell growth inhibition, and a new target (SA1575, of unknown function), as well as inhibition of cell wall biosynthesis, was reported.

Figure 13:
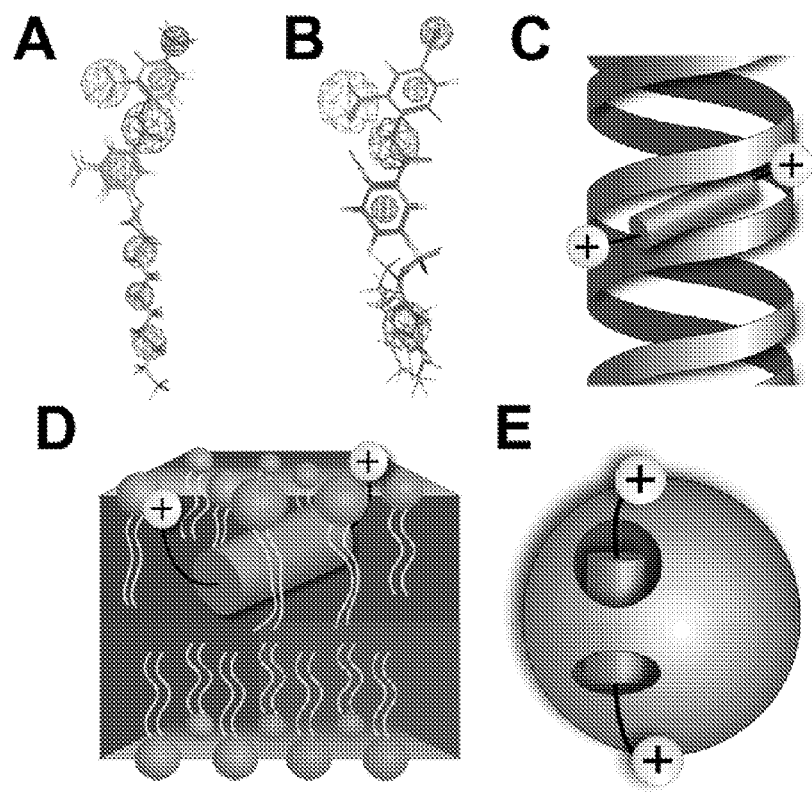
FIG. 13. UPPS as a missing link: Models and cartoons. (A) Pharmacophore model for UPPS inhibition by benzoic acids. (B) Pharmacophore model for *S. aureus* growth inhibition by benzoic acids. Common features are benzoic acid carboxylates with electron-withdrawing meta substituents; an x-y spacer; two aromatic features and more distal hydrophobic features (lower ends). (C) Cationic-hydrophobic-cationic inhibitor binding to DNA. (D) Cationic-hydrophobic-cationic inhibitor binding to anionic lipids in a membrane. (E) Cationic-hydrophobic-cationic inhibitor binding to a protein. See also Zhu et al., *Proc Natl Acad Sci USA* 2013, 110(1):123.

We find that a pharmacophore model (FIG. 13A) of seven potent benzoic acid UPPS inhibitors we synthesized (Scheme 2-1), is very similar to that obtained for *S. aureus* cell growth inhibition (FIG. 13B) using five structures reported by Larsen et al. (Scheme 2-2), making UPPS inhibition one likely mechanism for these inhibitors, in particular because they are already known to inhibit cell wall biosynthesis. In addition, we found that the compound 19 reported by Larsen et al. is a ~1-2 μM UPPS inhibitor (Table 1, above), consistent with a role in *S. aureus* growth inhibition.

Scheme 2-1. Structures of UPPS inhibitors used in pharmacophore modeling together with $IC_{50}$ values (in *S. aureus* UPPS inhibition).

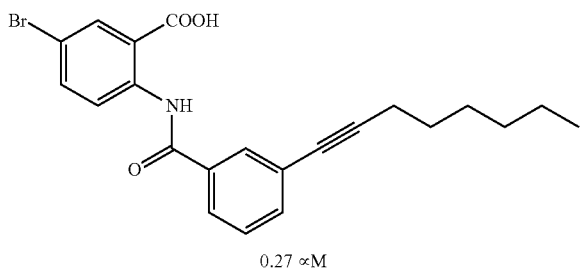

0.27 μM

-continued
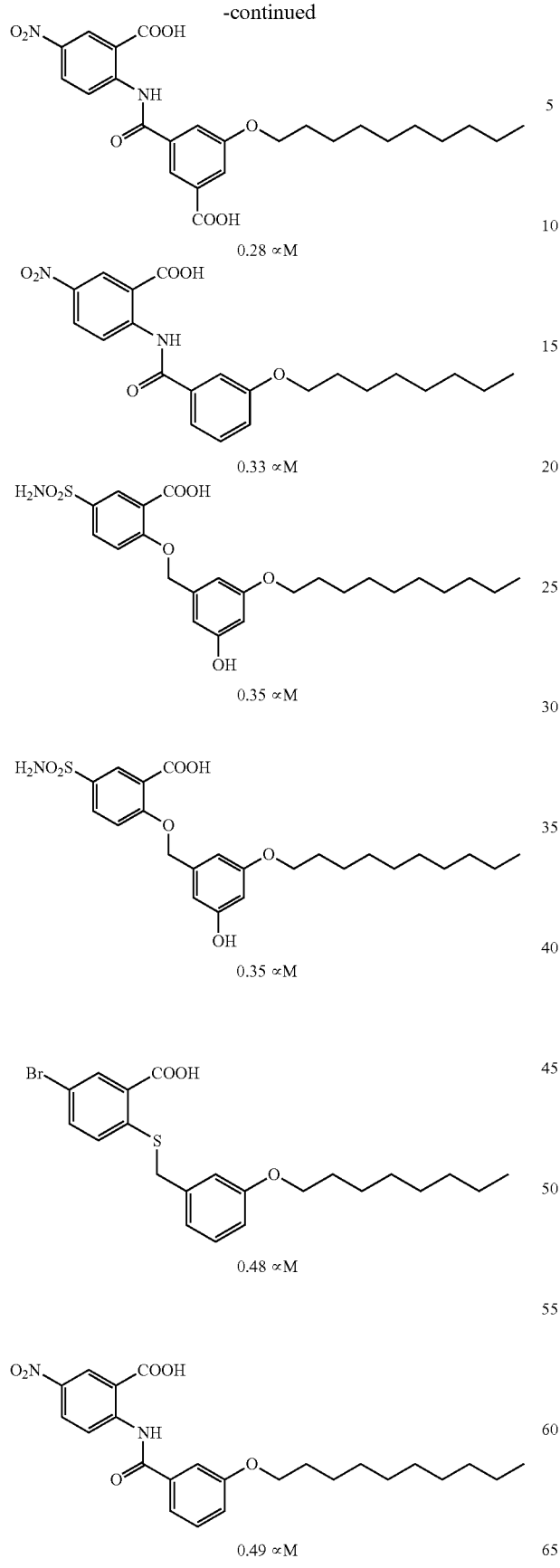
Scheme 2-2. Structures of Larsen et al.: *S. aureus* benzoic acid growth inhibitors used to construct the pharmacophore model in FIG. 13A, together with MIC values (in cell growth inhibition).
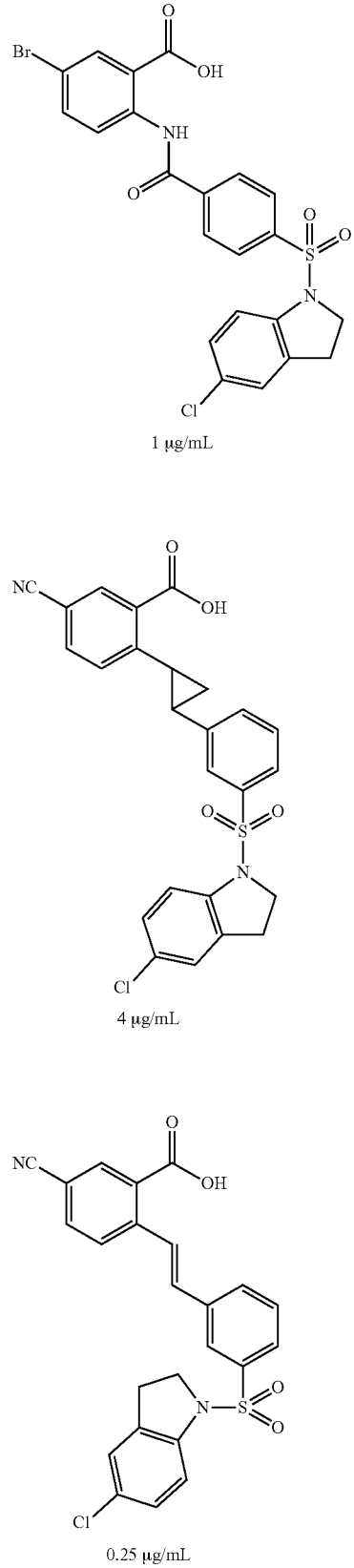

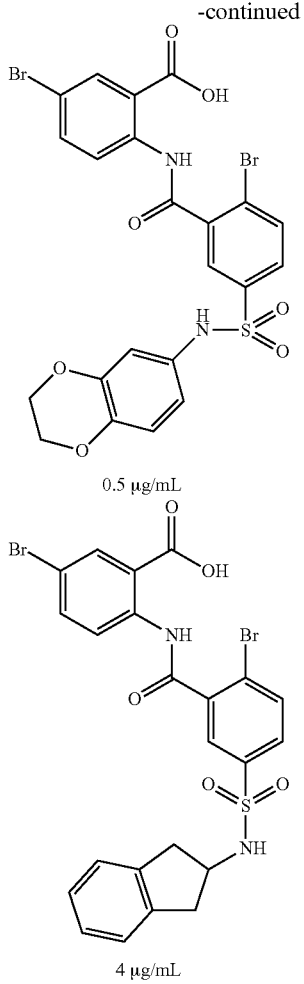

0.5 μg/mL

4 μg/mL

In addition to the benzoic/anthranilic acids, there is also interest in the mechanisms of action of bisamidines, such as 20 (Panchal et al., *Antimicrob Agents Chemother* 2009, 53(10):4283-4291; Butler et al., *Antimicrob Agents Chemother* 2010, 54(9):3974-3977), as well as of other cationic species such as 21 (Tew et al., *Acc Chem Res* 2010, 43(1):30-39). These and related compounds could bind to the minor groove of DNA, or that they could alter lipid bilayer structure, as illustrated schematically in FIGS. 13C and 13D. Based on our crystallographic (FIGS. 9C and 9D) and enzyme inhibition results it is clear, however, that in addition to these binding modes, "polar-hydrophobic-polar" inhibitors (such as 17 or 18) can also bind to proteins, as shown in the cartoon in FIG. 13E, with their polar headgroups located near polar protein residues (or at the protein-water interface), while their hydrophobic centers are buried inside the protein target (FIGS. 9C and D).

Notably, as with the benzoic acids, bisamidines such as 20 can inhibit cell wall biosynthesis and with 20 we find quite potent (470 nM) UPPS inhibition (Opperman et al. Poster Session, 50th Interscience Conference on Antimicrobial Agents and Chemotherapy, Sep. 12-15, 2010, Boston). The ability to inhibit UPPS in addition to, e.g., DNA and lipid membrane targeting likely contribute to the potent activity of these compounds and, in some cases, the lack of resistance observed experimentally. Other prenyl transferases, such as FPPS, may in some cases be targeted as well.

Figure 14:
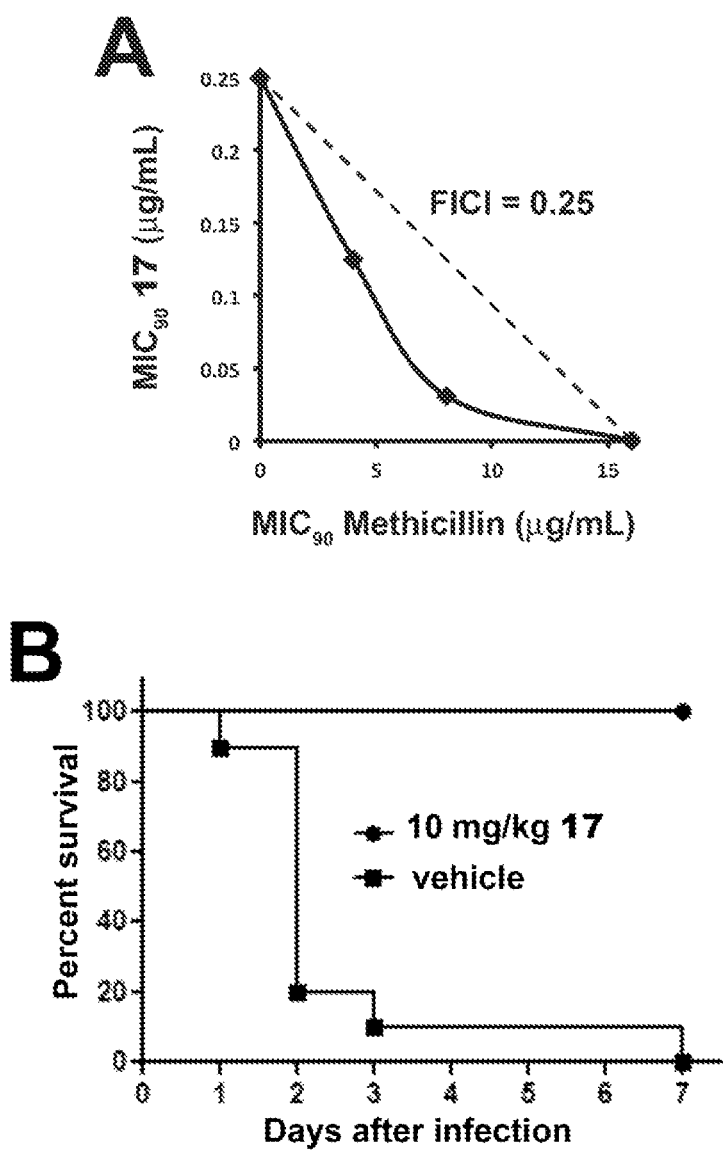
FIG. 14. In vitro synergy and in vivo results with 17. (A) Isobologram for 17 +methicillin inhibition of *S. aureus* (USA300) cell growth. FICI=0.25. (B) Activity of 17 in a mouse model of *S. aureus* (USA200) infection. Shown is one representative experiment repeated twice (n=10 mice per group per experiment). No mice in the group treated once daily with 10 mg/kg of 17 (3 doses total) died during either experiment.

Synergy and in vivo results. The UPPS inhibition results indicated the possibility of synergistic activity with downstream cell wall biosynthesis inhibitors, such as methicillin (see FIG. 1). This is indeed the case as shown in FIG. 14A, in which the isobologram (Berenbaum, *Pharmacol Rev* 1989, 41(2):93-141) for 17 + methicillin against a USA300 strain of MRSA is shown. A potent synergistic interaction was observed with a FICI (fractional inhibitory concentration index), defined as:

$$FICI = FIC_A + FIC_B = MIC_{90}(AB)/MIC_{90}(A) + MIC_{90}(BA)/MIC_{90}(B),$$

where, $FIC_A$, $FIC_B$ are the fractional inhibitory concentrations of drugs A and B, and $MIC_{90}$ (A), $MIC_{90}$ (B) are the $MIC_{90}$ values of the most effective combination of A or B in the presence of B or A. Using this method, FICI values of <0.5 represent synergism, >0.5 and <1.0 represent additivity, >1 and <2 represent an indifferent effect, while ≥2 represents drug antagonism (EUCAST Definitive Document E.Def 1.2, *Clin Microbiol Infect* 2000, 6(9):503-508). An FICI=0.25 thus represents strong synergism, opening up the probability of restoring drug sensitivity in drug-resistant strains.

For further information on FICI analysis, see: Eliopoulos and Moellering (1998). *Antimicrobial combinations. In Antibiotics in Laboratory Medicine,* 4th ed. Lorian, V.; Ed.; Williams & Wilkins Publising Co.: Baltimore,.330-396; and Singh et al. (2000). "Synergistic and additive killing by antimicrobial factors found in human airway surface liquid"; *Am J Physiol Lung Cell Mol Physiol* 2000, 279(5):L799-805.

Investigations were performed to determine if the compounds tested above are active in in vivo models of infection. In previous work, it has been found that, e.g., benzoic acids (such as 19) as well as tetramic acids (such as 6) have potent activity against bacteria. However, there have been no previous reports of in vivo activity, due perhaps to strong binding to plasma proteins. Because 17 had potent activity against UPPS (110 nM), we tested it in a mouse model of infection using the USA200 Sanger 252 (MRSA) strain of *S. aureus*. As can be seen in FIG. 14B, mice treated post-infection only with vehicle control all died, while mice treated with 17 (20/20 total, pooled results of 2 experiments) survived with no apparent adverse reactions.

Computational results: FTMap, Principal Component, and ROC/AUC Analyses. The results described above represent the development of a series of new UPPS inhibitors—drug candidates—some of which have potent activity in cells and a mouse infection model. From a structural perspective, a most surprising result was that the most potent inhibitors all bound to site-4, not the substrate site, site-1. In previous work on bisphosphonate UPPS inhibitors, we found that a wide range of bisphosphonates bound to site-1 and that enzyme inhibition and site-1 docking scores were highly correlated (Guo et al., *Proc Natl Acad Sci USA* 2007, 104(24):10022-10027). However, with all of the new (non-bisphosphonate) inhibitors described here, we find that binding to site-4 is the common structural denominator for ligands with high affinity. Other sites are also often occupied, with either two molecules binding, or one inhibitor spans two sites (sites 4 and 2, with the dicationic species).

Figure 15:
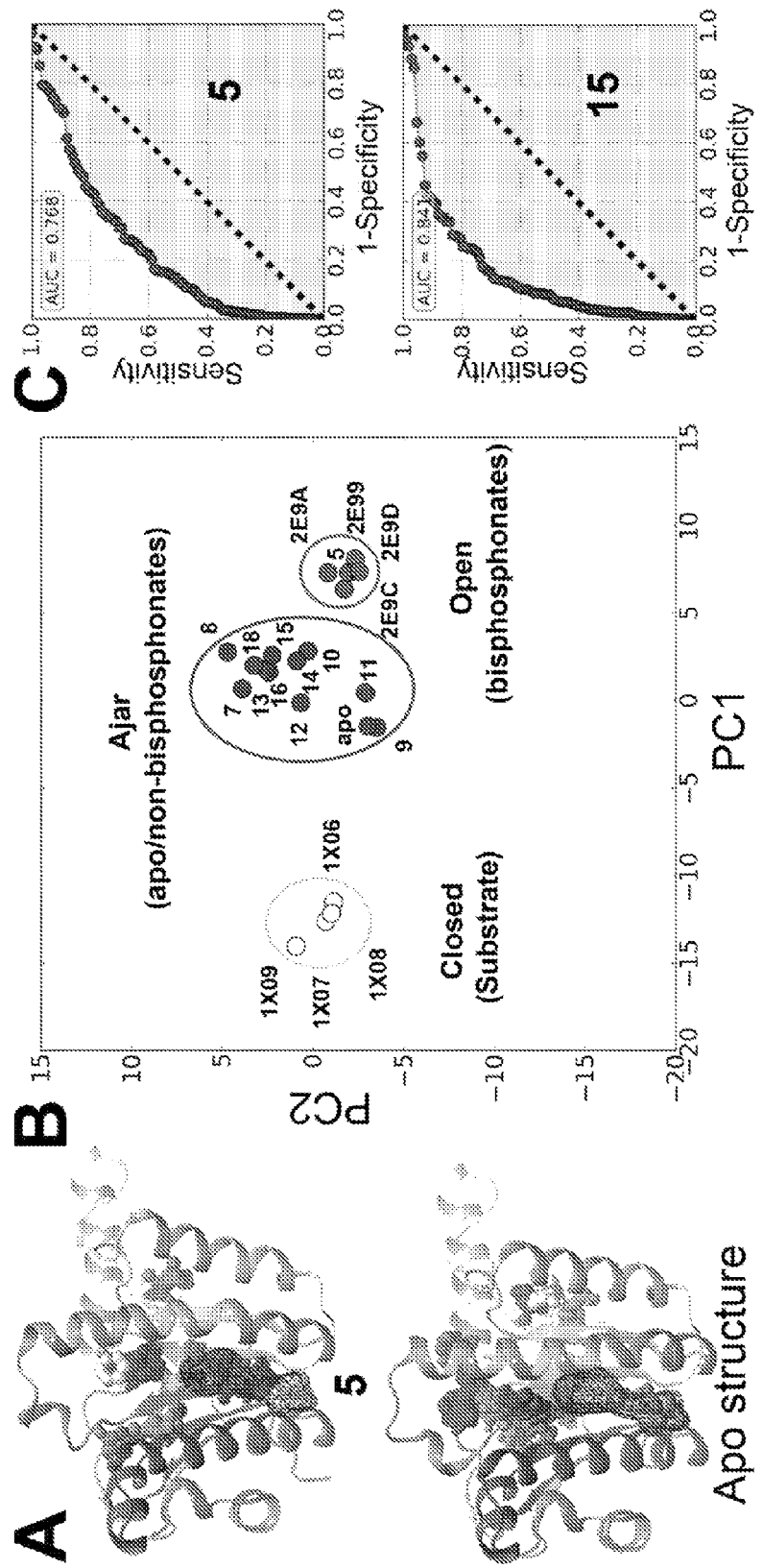
FIG. 15. Computational analysis of UPPS structural results. (A) FTMap computational solvent mapping of UPPS structures (PDB ID codes 2E98 and 3QAS) indicate that site 4 is druggable, in either inhibitor bound complexes, or unbound. UPPS is represented as a cartoon, small probes are spheres, central black wireframe outlines site 4. (B) PCA of *E. coli* UPPS structures. Substrate-bound structures (circle at left) are "closed"; bisphosphonates (circle at right) are "open"; the apo and non-bisphosphonate structures (central oval) are all "ajar"-slightly open (see Teng and Liang, "Structures, mechanisms and inhibitors of undecaprenyl diphosphate synthase: A cis-prenyltransferase for bacterial peptidoglycan biosynthesis"; *Bioorganic Chemistry* 2012, 43:51-57). (C) ROC-AUC analysis of most predictive UPPS structures in terms of initial enrichment for actives under 100 µM (see FIG. 17).

Site 4 is quite removed from the most flexible loop region (residues 72-82) of the active site, indicating that there may be less entropic costs due to constraining this loop, associated with inhibitor binding to site 4, rather than to sites 1-3, where the ligand directly contacts and restrains the loop. Site 4 is also predicted to be druggable when using the solvent mapping program FTMap (Ngan et al, "FTMAP: extended protein mapping with user-selected probe molecules"; *Nucleic Acids Res* 2012, 40(Web Server issue):W271-275), as shown in FIG. 15A, again supporting the concept that inhibitors that bind to site 4 are suitable therapeutic agents. With the new inhibitors, we also see that the global structures are quite similar to apo UPPS (FIG. 15B, middle oval), using principal component analysis (Grant et al., *Bioinformatics* 2006, 22(21):2695-2696). In FIG. 15B, the bisphosphonate inhibitors (circle at right) and substrate (circle at left) bound structures are altered to a greater extent from the apo form than are the new structures (middle oval). This indicates less induced-fit occurs on binding, which again will reduce any energetic costs associated with protein conformational changes upon binding.

Figure 16:
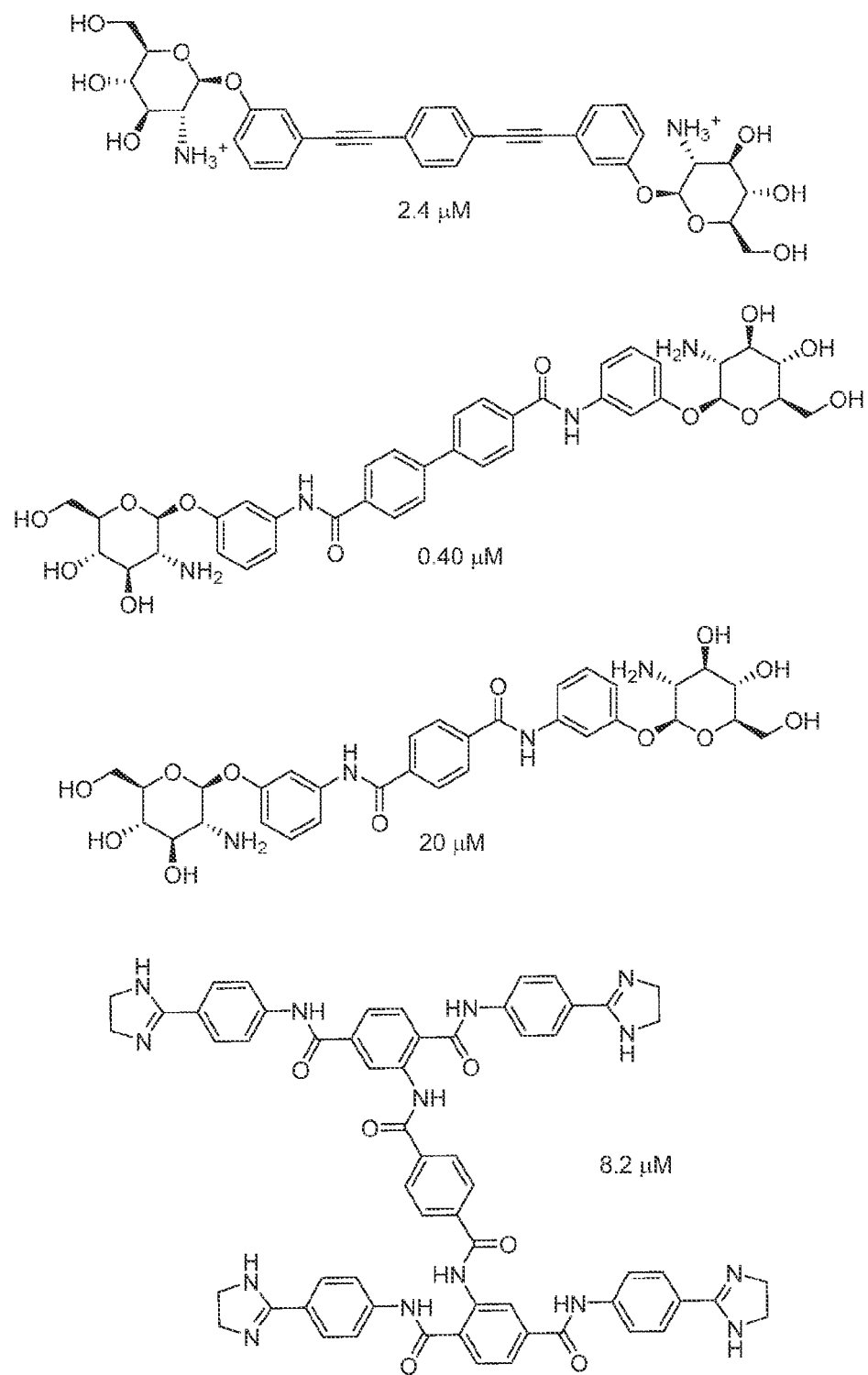
FIG. 16. Examples of screening library compounds used in ROC/AUC analysis. The $IC_{50}$ values are for *E. coli* UPPS inhibition.
Figure 16:
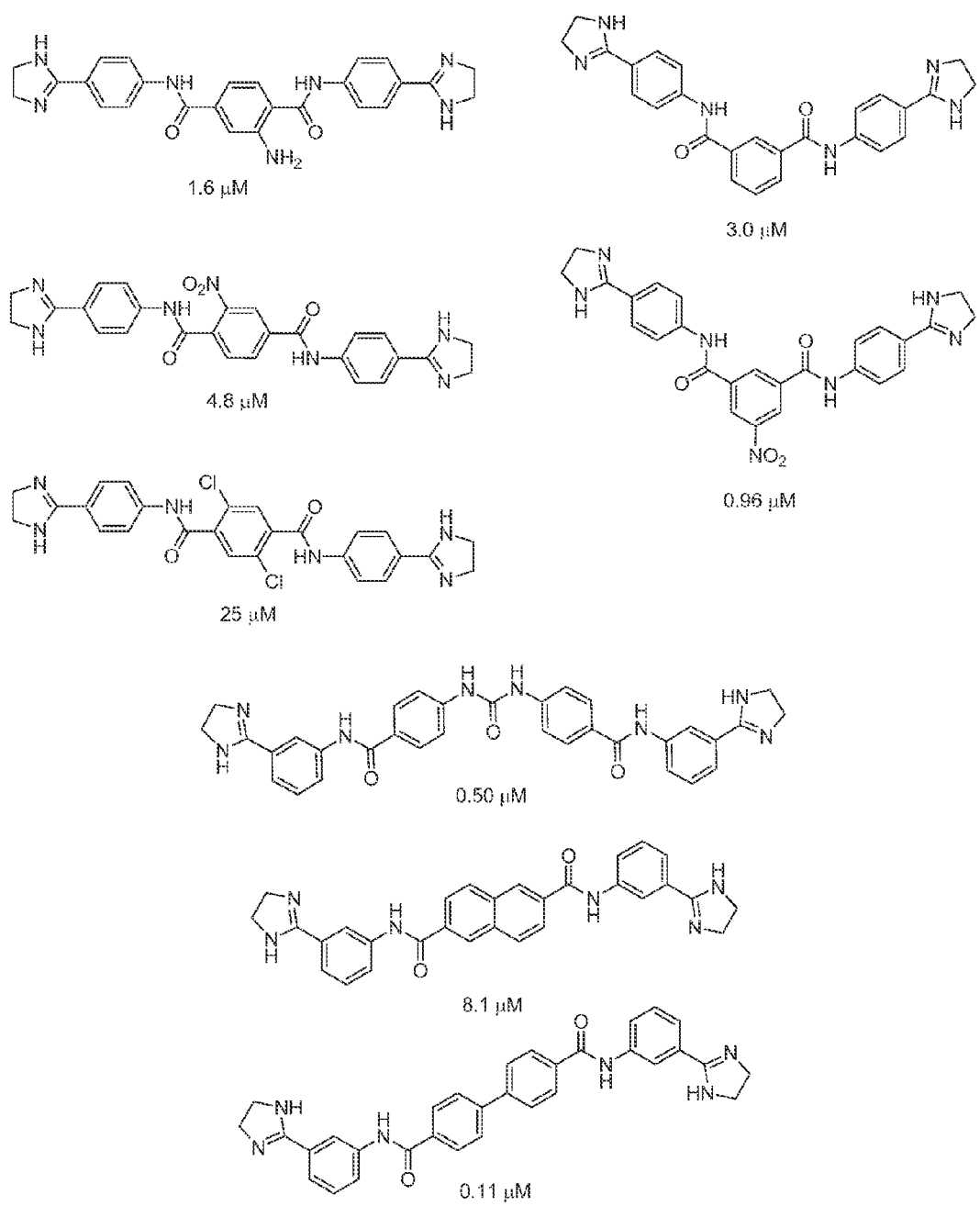
Figure 16:
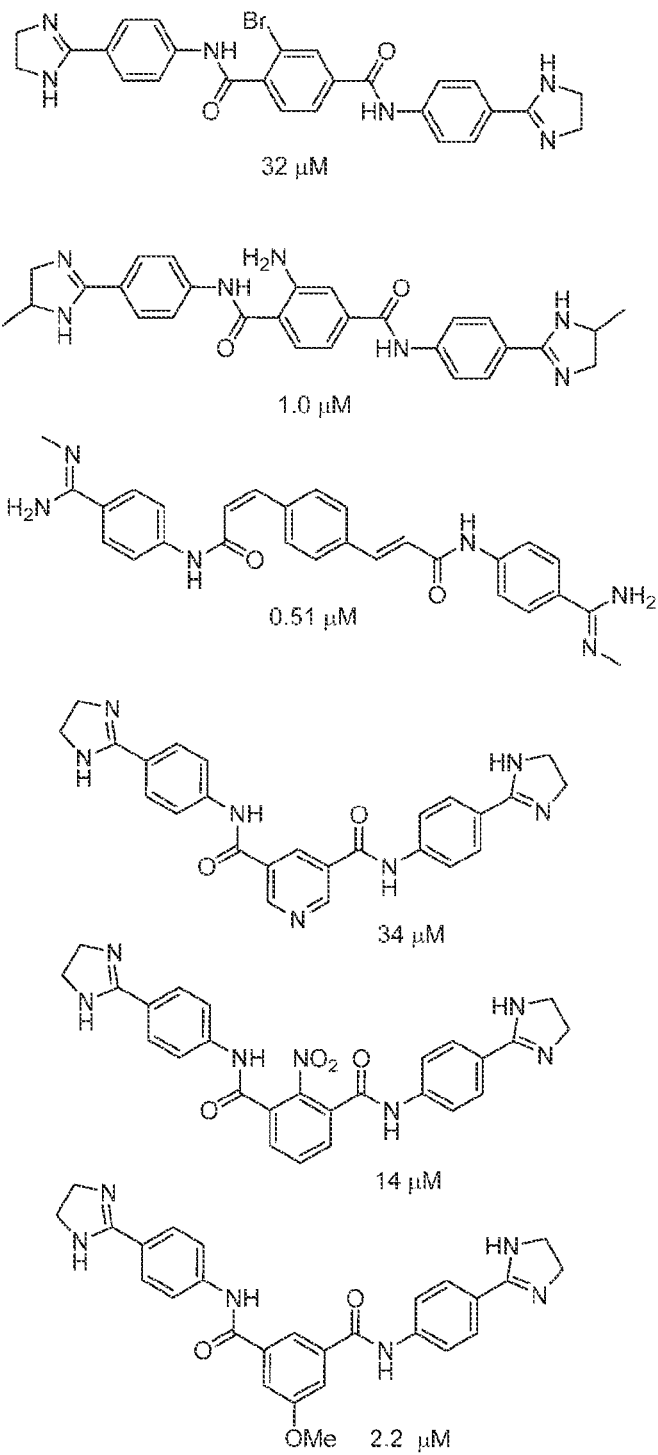
Figure 16:
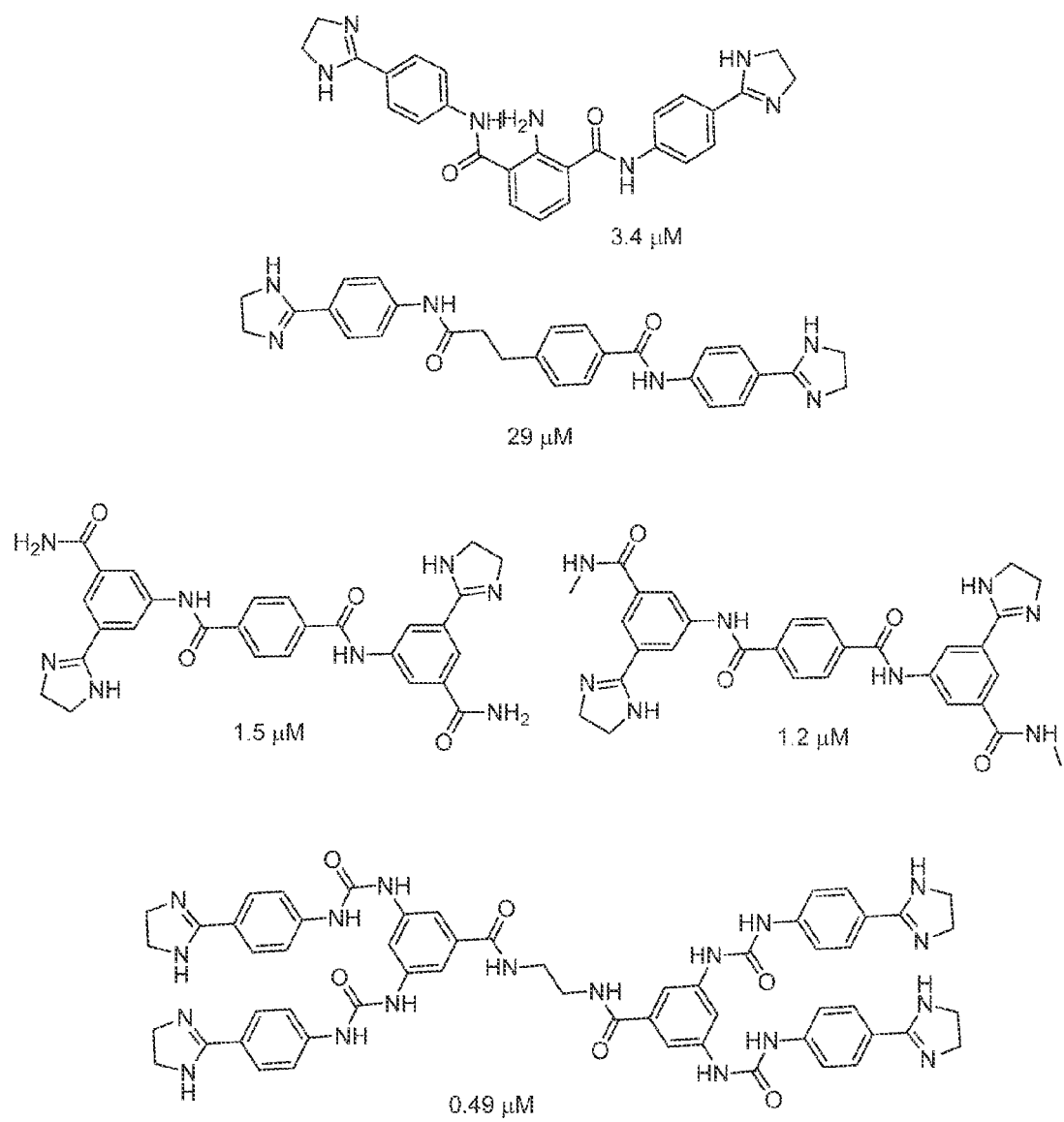
Figure 17:
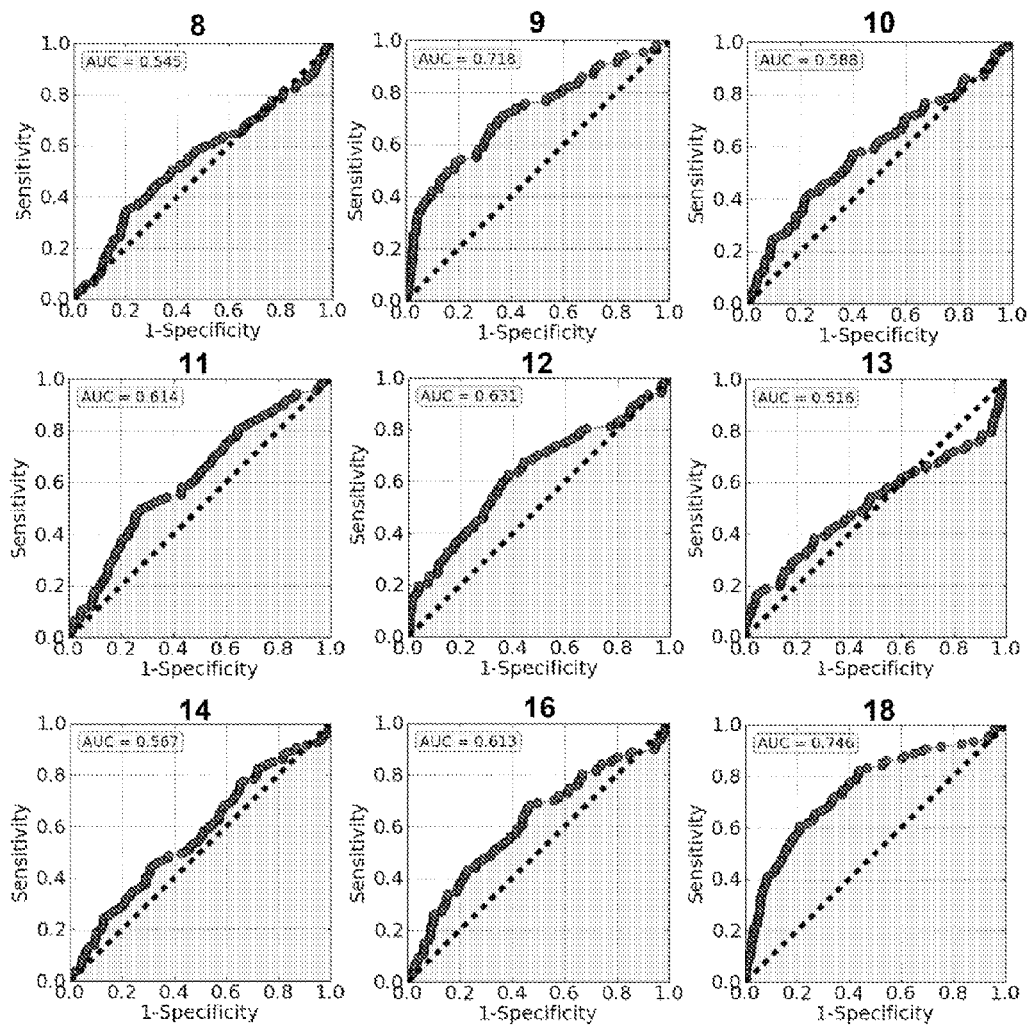
FIG. 17. ROC/AUC analyses for compounds shown in FIG. 16 based on the new crystal structures.

Finally, because many of these inhibitors were the result of virtual screening, we assessed the predictive nature of each structure using a receiver operating characteristic/area under the curve (ROC/AUC) approach (see Lee et al., "Optimization of high throughput virtual screening by combining shape-matching and docking methods"; *J. Chem. Inform. & Model.* 2008, 48(3):489-497) with a 112 compound screening dataset (see FIG. 16 for several of the compounds). Enrichment results are shown in FIG. 15C and FIG. 17. Good results (AUC=0.768) are obtained when using the "open" structure containing 5 bound to sites 1-4, but a superior result is obtained using compound 15 (PDB ID code 4H3A), an "ajar" (FIG. 15B) or partially closed structure in which only site 4 is occupied (FIG. 8C, bottom) where AUC=0.841. Taken together, these results strongly support the importance of developing compounds that bind to site 4 as UPPS inhibitors and drug candidates, and that computational models based on these new structures can significantly enrich the hit rate.

Conclusions. The results we have described above are of interest for several reasons. First, we obtained the x-ray structures of ten new UPPS inhibitors covering a diverse range of structures: benzoic acids, diketoacids, an aryl phosphonate, a bisamidine and a bisamine. Surprising results include that both cationic as well as anionic compounds were inhibitors, the cationic species having an unusual polar-hydrophobic-polar structural motif. Second, we find evidence that occupancy of site 4 (not the FPP substrate site, site 1) correlates with the potent activity of these inhibitors, and that site 4 is druggable. Third, we find that the cationic (bisamidine and a bisamine) inhibitors span both sites 2 and 4, with their polar groups at or near the protein/water interface, while their hydrophobic domains are buried. This result is of particular importance since this motif is very similar to that proposed to be important for DNA and lipid membrane binding with structurally related inhibitors, leading to the concept that such compounds may have multiple targets (including UPPS), thereby increasing potency. We also find that a closely related biphenyl analog (17) inhibits UPPS at ~100 nM levels, has a MIC$_{90}$ of 0.25 µg/mL, and strongly synergistic activity (FICI=0.25) with methicillin, in an MRSA strain otherwise resistant to the antibiotic. In addition, this compound shows clear therapeutic activity in a mouse model of infection. Finally, we discovered that anthranilic acids, known to be potent inhibitors of *S. aureus* growth that target cell wall biosynthesis, also target bacterial UPPS. Taken together, these results open up new routes to anti-infective therapies targeting bacterial isoprenoid biosynthesis and indicate that drug leads that target DNA and lipid membrane structure can also target bacterial cell wall biosynthesis, via UPPS inhibition.

Methods. EcUPPS and SaUPPS were expressed and purified as described previously (Durrant et al., *Chem Biol Drug Des* 2011, 78(3):323-332). UPPS inhibition assays were carried out as described previously, and UPPS/inhibitor crystals were obtained via soaking as described previously (Guo et al., *Proc Natl Acad Sci USA* 2007, 104(24):10022-10027). Structure determinations and refinements were carried out as described below in Example 3. For the eleven structures reported, the resolution was on average 1.88 Å (±0.29 Å) and R$_{free}$ was on average 24.6% (±3.9%). Full synthesis and characterization details for all compounds investigated crystallographically are provided in Example 1 above. In vivo experiments used female BALB/c mice infected intraperitoneally with *S. aureus* (USA200), as described in detail in Example 3 below. Bacterial cell growth inhibition assays were carried out as described previously (Zhang et al., *ACS Med Chem Lett* 2012, 3(5):402-406).

Example 3

Enzyme Inhibitor Purification and Analysis

*E. coli* UPPS Expression and Purification. The *E. coli* UPPS plasmid was provided by Professor Andrew H.-J Wang. The purification of UPPS from *E. coli* followed the published protocol with modifications (Pan et al., *Biochemistry* 2000, 39(35):10936-10942). The plasmid was transformed into *E. coli* BL21 (DE3) cells (Novagen) for expression. A single transformant was grown up overnight at 37° C. in LB medium containing 100 µg/mL ampicillin. The 50 mL overnight cultures were transferred to 2 L fresh LB medium containing 100 µg/mL ampicillin and allowed to grow to OD$_{600}$=0.6 before induction with 1 mM IPTG. The cultures were induced for 4 h at 37° C. and harvested by centrifugation. Cell pellets were suspended in 60 mL buffer (25 mM Tris-HCl, pH 7.5 and 150 mM NaCl), followed by pulse sonication. The lysate was centrifuged and the cell debris discarded. For purification, the cell free extract was loaded into a 20 mL Ni-NTA column pre-equilibrated with 25 mM Tris-HCl (pH 7.5) and 150 mM NaCl. The column was washed with 30 mM imidazole-containing buffer. The His-tagged UPPS was eluted with a 0% to 100% gradient buffer (25 mM Tris-HCl, pH 7.5, 150 mM NaCl and 300 mM imidazole). The protein solution was dialyzed against 3×2 L buffer (25 mM Tris-HCl, pH 7.5 and 150 mM NaCl). The His-tagged UPPS was then digested with FXa protease to remove the His-tag. The solution was then loaded onto Ni-NTA. The UPPS in the flow through (25 mM Tris-HCl, pH 7.5, 150 mM NaCl and 30 mM imidazole) was pure as evidenced by to SDS-PAGE, and was dialyzed into buffer (25 mM Tris, pH 7.5 and 150 mM NaCl) for storage. The final concentration was determined by using a Bradford protein assay kit.

*S. aureus* UPPS Expression and Purification. The gene encoding UPPS was amplified from a plasmid (Durrant et al., *Chem Biol Drug Des* 2011, 78(3):323-332) containing the *S. aureus* UPPS gene. The forward primer was 5' GTA TTG AGG GTC GCA TGT TTA AAA AGC TAA TAA ATA AAA AGA ACA C 3' (SEQ ID NO: 2), and the reverse primer was 5' AGA GGA GAG TTA GAG CCC TAC TCC TCA CTC 3' (SEQ ID NO: 3). The amplified UPPS gene was purified and ligated into a pET-32 Xa/LIC vector (Novagen, Madison, WI, USA). The plasmid with the *S. aureus* UPPS gene was subsequently expressed in *E. coli* BL 21 (DE3) cells (Novagen). The protocol for expression and purification of *S. aureus* UPPS was the same as that for *E. coli* UPPS.

X-Ray Crystallography. Native *E. coli* UPPS crystals for use in soaking were obtained by using the hanging-drop method (Hampton Research, Laguna Niguel, Calif.) by mixing 1 µl of UPPS protein solution (~14 mg/ml UPPS in 25 mM Tris-HCl, pH 7.5 and 150 mM NaCl) with 1 µl of mother liquor (25 mM Tris-HCl, pH 7.5, 150 mM NaCl and 5% PEG 2-4K) and then equilibrating with 400 µL mother liquor at room temperature. Tetragonal crystals appeared in 2 days and were then soaked in a cryoprotectant solution (25 mM Tris-HCl, pH 7.5, 150 mM NaCl, 30% EG and 5% PEG 35K) containing 1-5 mM inhibitors for 1 day.

S. aureus UPPS crystals with FPP were obtained by using the hanging-drop method (Hampton Research, Laguna Niguel, Calif.) by mixing 1 µl of UPPS protein solution (~5 mg/ml UPPS in 1.5 mM $MgCl_2$, 1.5 mM FPP, 25 mM Tris-HCl, pH 7.5 and 150 mM NaCl) with 1 µL of mother liquor (100 mM NaMES, pH 6.5, 200 mM $(NH4)SO_4$, and 25% PEG MME 5K) and then equilibrating with 400 µL mother liquor at room temperature. Bi-pyramidal crystals appeared overnight.

X-ray diffraction data for both EcUPPS and SaUPPS were collected at the Life Science Collaborative Access Team (LS-CAT) 21-ID-D (F or G) at the Advanced Photon Source of Argonne National Laboratory. Diffraction data were processed and scaled by using the program HKL3000 (HKL Research Inc., Charlottesville, Va., USA). The statistics for data collection are listed in Table 2 (FIG. 6) and 3B (see Example 2 above).

The structures of the UPPS-complexes were determined by using a model prepared from the UPPS/BPH-629 complex structure (PDB ID 2E98) with ligands and solvent removed. Structure refinements were carried out by using Refmac (Murshudov et al., *Acta Crystallogr D Biol Crystallogr* 1997, 53(Pt 3):240-255; Potterton et al., *Acta Crystallogr D Biol Crystallogr* 2003, 59(Pt 7):1131-1137), Phenix (Adams et al., (2010) PHENIX: a comprehensive Python-based system for macromolecular structure solution. *Acta Crystallogr D Biol Crystallogr* 2010, 66(Pt 2):213-221), and Coot (Emsley and Cowtan, *Acta Crystallogr D Biol Crystallogr* 2004, 60(Pt 12 Pt 1):2126-2132). All structure figures were prepared by using PyMOL (WL D (2008) *The PyMOL Molecular Graphics Systems*. DeLano Scientific LLC, Palo Alto, Calif., USA).

UPPS Inhibition Assays. *E. coli* UPPS and *S. aureus* UPPS inhibition assays were carried out as described previously (Durrant et al., *Chem Biol Drug Des* 2011, 78(3): 323-332). Briefly, the condensation of FPP with IPP catalyzed by UPPS was monitored by using a continuous spectrophotometric assay (Webb, *Proc Natl Acad Sci USA* 1992, 89(11):4884-4887) in 96 well plates with 200 µL reaction mixtures containing 400 µM MESG, 350 µM IPP, 35 µM FPP, 25 mM Tris-HCl (pH 7.5), 0.01% Triton X-100 and 1 mM $MgCl_2$. The $IC_{50}$ values were obtained by fitting the inhibition data to a standard rectangular hyperbolic dose-response function in GraphPad PRISM 4.0 software (Graphpad Software, San Diego, Calif.). The $IC_{50}$ values for the most active hits were verified by using a radiometric assay (Li et al., *J Biomol Screen* 2003, 8(6):712-715) with 2.5 µM FPP, 25 µM [$^{14}$C] IPP and 0.01% Triton X-100.

Computational Aspects. Pharmacophore models were constructed in MOE (Molecular Operating Environment (MOE), Chemical Computing Group, Inc.: Montreal, Quebec, 2006) using the consensus pharmacophore module. The Glide docking algorithm at the XP level was used to perform all docking calculations with UPPS (see Friesner et al., *J Med Chem* 2006, 49(21):6177-6196). X-ray structures were prepared with the protein preparation wizard using standard parameters (Schrödinger Suite 2011 Protein Preparation Wizard; Epik version 2.2, Schrödinger, LLC, New York, N.Y., 2011; Impact version 5.7, Schrödinger, LLC, New York, N.Y., 2011; Prime version 2.3, Schrödinger, LLC, New York, N.Y., 2011). Compounds were prepared with Ligprep using standard parameters (LigPrep, version 2.5, Schrödinger LLC: New York, N.Y., 2011). For the calculation of the ROC/AUC curves, 112 *E. coli* UPPS inhibitors with $IC_{50}$<100 µM were combined with the Schrödinger decoy library of 1000 compounds (having an average molecular weight of 400 Daltons) (Friesner et al., *J Med Chem* 2004, 47(7):1739-1749; Halgren et al., *J Med Chem* 2004, 47(7):1750-1759). Compounds from this combined library were ranked by their Glide XP docking scores and the AUC calculated.

PCA was performed using the monomer that had the most ligands present or, if not applicable, the most residues resolved. An invariant "core" of Cα atoms was first determined, then structures were aligned with the core and PCA analysis performed using BIO3D (Grant et al., *Bioinformatics* 2006, 22(21):2695-2696). The principal components plotted in FIG. 15B describe orthogonal eigenvectors with maximal variance. Hierarchical clustering was performed based on the Euclidian distance matrix of the first two principal components, then reduced to 3 groups of related "clusters" (Murtagh (1985) *Multidimensional Clustering Algorithms* (Physica-Verlag)).

Cell growth inhibition. The growth of *S. aureus* (USA300 strain) and determination of MIC values were as described previously (Molohon et al., *ACS chemical biology* 2011, 6(12):1307-1313). *E. coli* growth and construction of isobolograms were also carried out basically as described previously (Leon et al., *J Med Chem* 2006, 49(25):7331-7341).

In vivo experiments. Mice were infected intraperitoneally with $10^9$ cfu MRSA (strain Sanger 252) suspended in 4% hog gastric mucin. At 1 hour after infection, the mice were divided into 2 groups (n=10 per group) and treated intraperitoneally with either 17 (10 mg/kg) suspended in water or water alone (vehicle control). Treatment was continued once daily for 2 more days. Mortality was monitored twice daily.

Example 4

Enzyme Inhibition and Compound Preparation

Additional enzyme inhibitors of the invention include the compounds described in this example, several of which illustrate a variety of $R^1$ groups of the invention, as well as optional substitutions, such as N-ethyl bisphosphonates, which can be $R^1$ or $R^2$ group substituents. As with each of the structures described herein, the phenyl substitution patterns can be ortho, meta, or para to the central phenyl or other central structure or linker.

| pH | logD |
|---|---|
| 1.50 | −1.70 |
| 5.00 | −1.65 |
| 6.50 | −0.80 |
| 7.40 | 0.67 |
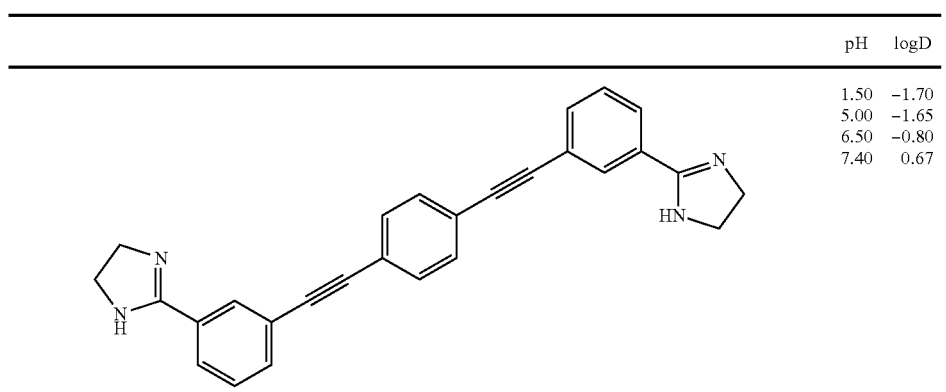
(V.2)
| pH | logD |
|---|---|
| 1.50 | 0.65 |
| 5.00 | 0.68 |
| 6.50 | 1.10 |
| 7.40 | 1.84 |
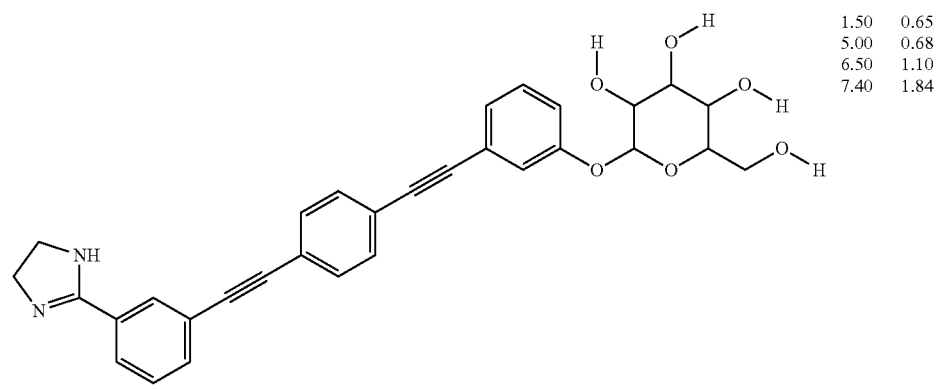
(V.3)
| pH | logD |
|---|---|
| 1.50 | 1.04 |
| 5.00 | −0.43 |
| 6.50 | −0.46 |
| 7.40 | −0.52 |
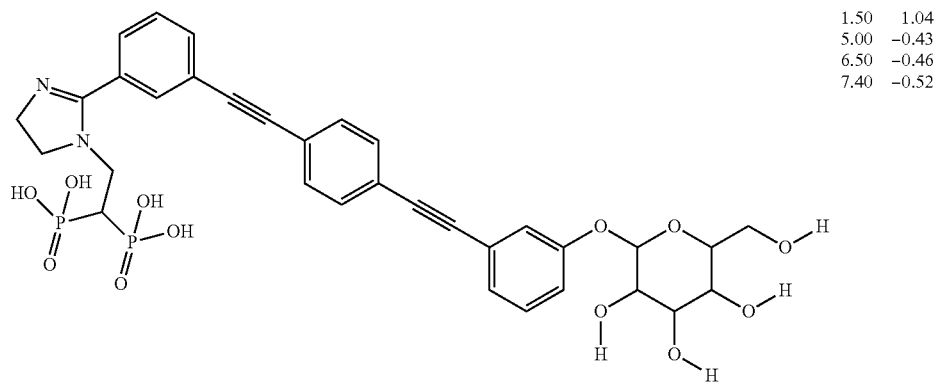
(V.4)

Further examples of inhibitors include compounds of Formula VI:

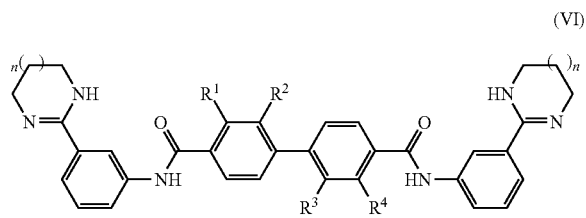

(VI)

wherein

R¹, R², R³, and R⁴ are each independently hydrogen, alkyl, alkoxy, hydroxy, amino, nitro, halo, or an optionally substituted phenylamide; and n is 0, 1, or 2;

or a salt thereof.

In some embodiments, the compound of Formula VI is a compound of Formula VI.A, VI.B, or VI.C:

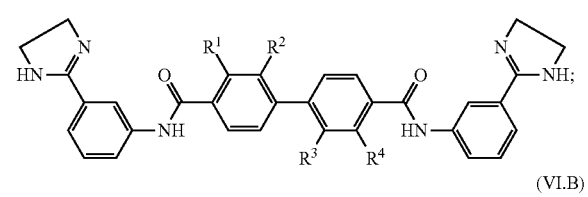

(VI.A)

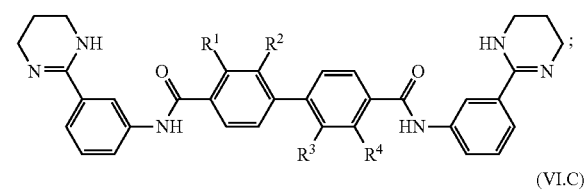

(VI.B)

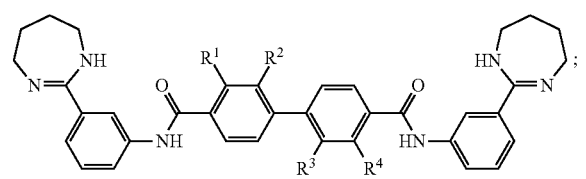

(VI.C)

wherein R¹, R², R³, and R⁴ are as defined for Formula VI. Specific examples of compounds of Formula VI.A and VI.B that have been prepared include compounds summarized by Table 4.1.

TABLE 4.1

Various compounds of the invention.

| Cmpd. No. | R¹ | R² | R³ | R⁴ |
|---|---|---|---|---|
| 4.1 | H | H | H | H |
| 4.2 | F | H | H | H |
| 4.3 | F | H | Me | H |
| 4.4 | F | H | F | H |
| 4.5 | F | H | OH | H |
| 4.6 | F | H | OMe | H |
| 4.7 | F | H | H | OMe |
| 4.8 | F | H | H | NO₂ |
| 4.9 | Cl | H | H | H |

TABLE 4.1-continued

Various compounds of the invention.

| Cmpd. No. | R¹ | R² | R³ | R⁴ |
|---|---|---|---|---|
| 4.10 | Cl | H | H | F |
| 4.11 | OH | H | H | H |

The invention also provides compounds of Formula IV.A:

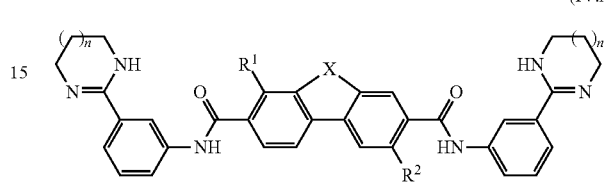

(IV.A)

wherein

X is O, NH, S, or SO₂;

n is 0, 1, or 2;

R¹ is H, halo, alkyl, alkoxy, or NO₂;

R² is H, halo, alkyl, alkoxy, or NO₂;

or a salt thereof. Specific examples of R¹ include H, Cl, F, Me, OMe, and NO₂. Specific examples of R² include H, Cl, F, Me, OMe, and NO₂.

The invention further provides compounds of Formula IV.B:

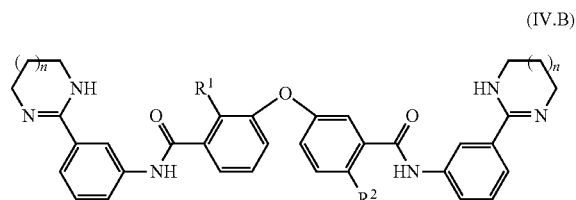

(IV.B)

wherein n is 0, 1, or 2;

R¹ is H, halo, alkyl, alkoxy, or NO₂;

R² is H, halo, alkyl, alkoxy, or NO₂;

or a salt thereof. Specific examples of R¹ include H, Cl, F, Me, OMe, and NO₂. Specific examples of R² include H, Cl, F, Me, OMe, and NO₂. The central oxygen linker can also be located para to one or both amide carbonyl groups in Formula IV.A.

The invention further provides compounds of Formula IV.C:

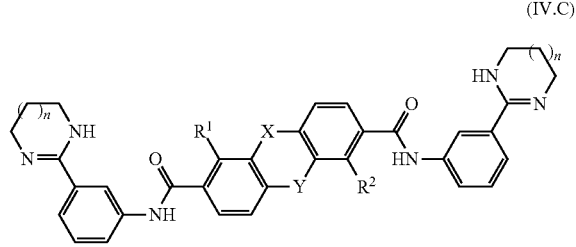

(IV.C)

wherein n is 0, 1, or 2;
X is O, NH, S, or absent;
Y is O, NH, S, or a direct bond;
$R^1$ is H, halo, alkyl, alkoxy, or $NO_2$;
$R^2$ is H, halo, alkyl, alkoxy, or $NO_2$;

or a salt thereof. Specific examples of $R^1$ include H, Cl, F, Me, OMe, and $NO_2$. Specific examples of $R^2$ include H, Cl, F, Me, OMe, and $NO_2$. Both X and Y can also be absent, thereby providing fused benz groups (i.e., a central naphthyl group).

Figure 18:
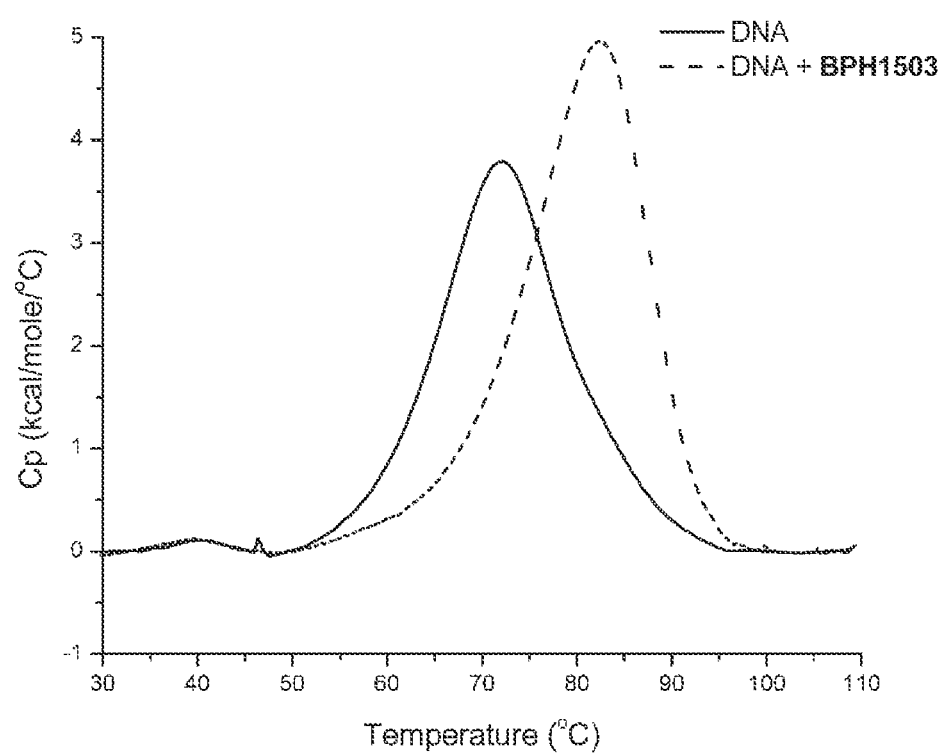
FIG. 18. Results of differential scanning calorimetry (DSC) experiments for DNA binding with BPH-1503. Melting curves are shown for a synthetic DNA dodecamer duplex d(CGCGAATTCGCG)2 ("CGCGAATTCGCG" disclosed as SEQ ID NO: 1) at 1 mM concentration (dashed line) and for an identical DNA solution with 1 mM BPH-1503 added. A shift in Tmax (the maximum of the $C_p$ vs. T thermogram) of ~10° C. indicates strong DNA binding with BPH-1503. The DSC experiments were performed on a Microcal VP-DSC instrument. The scans covered the range from 30 to 110° C. at a scan rate of 90° C/h. The DSC thermograms were analyzed using Origin 7.1 (Massachusetts, USA). Buffer vs. buffer (10 mM MES, pH6.2, 1 mM EDTA and 200 mM NaCl) scans were used for baseline correction.

In one specific embodiment, a compounds of Formula IV is the compound BPH-1503:

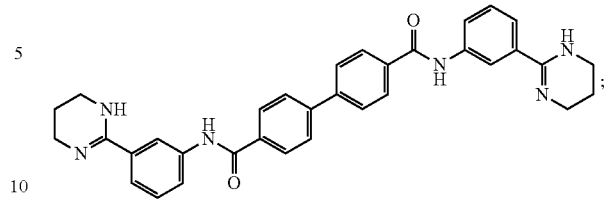
(BPH-1503)

or a salt thereof. BPH-1503 has cell and UPPS activity and binds to DNA. An x-ray crystal structure of BPH-1503 bound to DNA was prepared. DNA binding data for BPH-1503 is shown in FIG. 18.

Example 6

Preparation of Compounds having 5-, 6-, and 7-Membered Amidines $N^4,N^{4'}$Bis(3-(4,5-Dihydro-1H-Imidazol-2-yl)Phenyl)-[1,1'-Biphenyl]-4,4'-Dicarboxamide.

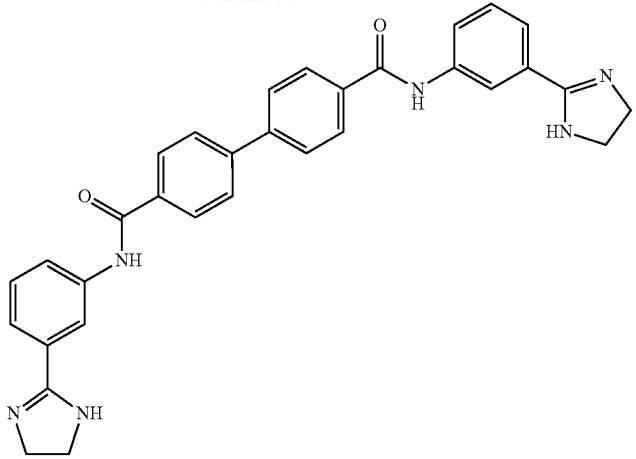

To a mixture of 4,4'-diphenyl dicarbonylchloride (1.39 g, 5 mmol), 3-aminobenzonitrile (1.18 g, 10 mmol) in anhydrous THF (20 mL) was added Et$_3$N (2.1 mL, 15 mmol) and the mixture was stirred at room temperature overnight. After filtration, the white solid was washed with water (20 mL) and ethyl acetate (10 mL) and then dried. Sodium hydrosulfide hydrate (100 mg), ethylenediamine (2 mL), and dimethylacetamide (10 mL) were then added and stirred overnight at 140° C. Upon removal of the solvent, the solid was washed thoroughly with water and then ethyl acetate (10 mL). To the suspension of the crude product in 10 mL of water were added two equivalents of methyl sulfonic acid. Removal of water afforded product as its methanesulfonic acid salt (1.44 g, 40%). $^1$H NMR (DMSO-D$_6$, 500 MHz) δ: 10.68 (s, 2 H), 10.52 (s, 4 H), 8.50 (s, 2 H), 8.12 (d, J=9.0 Hz, 4 H), 8.02-7.98 (m, 2 H), 7.96 (d, J=9 Hz, 4 H), 7.68-7.58 (m, 4 H), 4.00 (s, 8 H), 2.36 (s, 6 H). $^{13}$C NMR (DMSO-D$_6$, 125 MHz) δ: 166.1, 166.1, 143.0, 140.6, 134.4, 130.6, 129.2, 127.7, 127.0, 124.3, 123.5, 120.8, 45.3. HRMS (ESI): m/z [M+H]$^+$ calculated for C$_{32}$H$_{29}$N$_6$O$_2$: 529.2361, found: 529.2352.

A similar procedure as described for the preparation of 5-membered amidines (above) was used for 6-membered amidines, using 1,3-propylenediamine instead of 1,2-ethylenediame, as summarized in Scheme 6.1 below.

Scheme 6.1

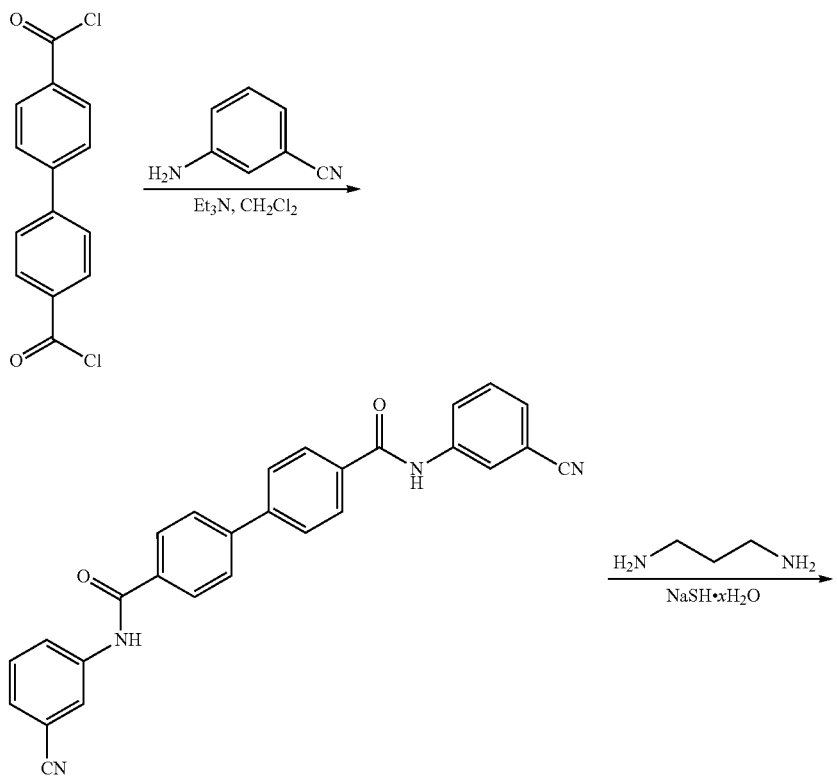

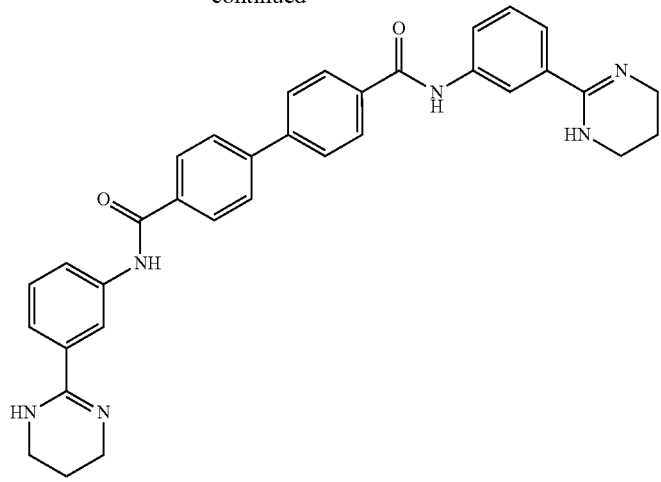
BPH-1503
A similar procedure as described for the preparation of 5-membered amidines (above) was used for 7-membered amidines, using 1,4-butylenediamine instead of 1,2-ethylenediame, as summarized in Scheme 6.2 below.
Scheme 6.2
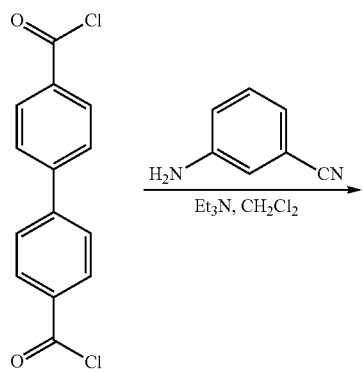
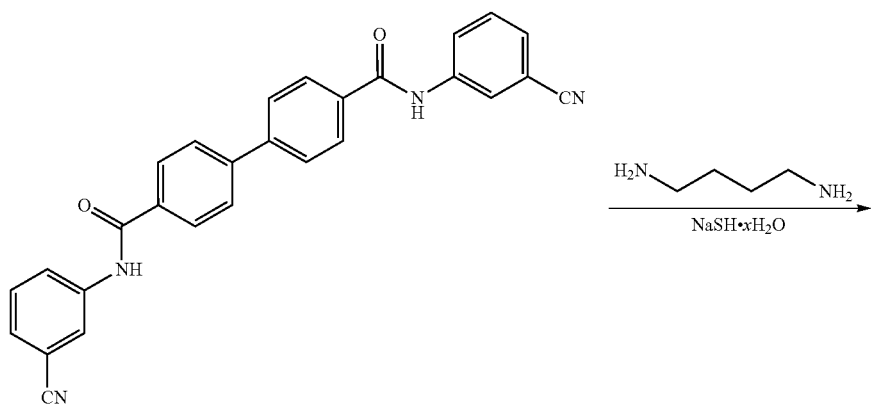

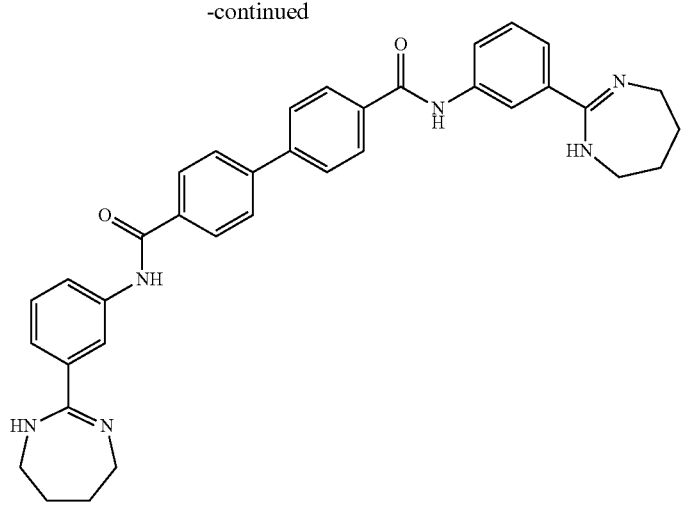

These methods for preparing 5-, 6-, and 7-membered bis-amidines are general and can be applied to any corresponding intermediate having aryl or heteroaryl nitrile moieties. Accordingly, any compound described or illustrated herein having one or more 5-membered amidines can also be provided as the compound with the corresponding 6-membered or 7-membered amidine moieties.

Example 7

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution | q.s. |
| (pH adjustment to 7.0-7.5) | |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution | q.s. |
| (pH adjustment to 7.0-7.5) | |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine | q.s. |
| (pH adjustment to 5-7) | |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method of killing or inhibiting the growth of methicillin-resistant *Staphylococcus aureus* (MRSA) comprising contacting the MRSA with an effective lethal or inhibitory amount of a compound of Formula V that binds to site 4 of bacterial undecaprenyl diphosphate synthase (UPPS), and further comprising contacting the MRSA with an effective lethal or inhibitory amount of methicillin, and the compound of Formula V is:

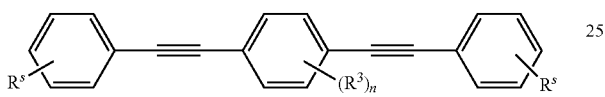

(V)

wherein each $R^S$ is independently a saccharide moiety;

each $R^3$ is independently hydrogen, alkyl, alkoxy, hydroxy, amino, nitro, halo, or an optionally substituted phenylamide;

n is independently 1, 2, 3, or 4; and the molecular weight is at least about 300 and less than about 1,200;

or a salt or solvate thereof, thereby killing or inhibiting the growth of the MRSA.

2. The method of claim 1 wherein the compound of Formula V is:

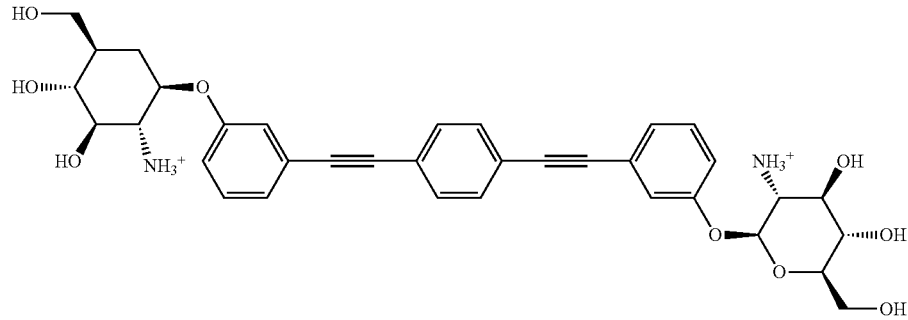 [SMILES: [NH3+][C@@H]1[C@@H](O)[C@H](O)[C@@H](CO)C[C@H]1Oc1cccc(C#Cc2ccc(C#Cc3cccc(O[C@@H]4O[C@H](CO)[C@@H](O)[C@H](O)[C@H]4[NH3+])c3)cc2)c1]

or a salt or solvate thereof.

* * * * *

UNITED STATES PATENT AND TRADEMARK OFFICE
CERTIFICATE OF CORRECTION

PATENT NO. : 9,951,097 B2
APPLICATION NO. : 14/649153
DATED : April 24, 2018
INVENTOR(S) : Wei Zhu et al.

Page 1 of 1

It is certified that error appears in the above-identified patent and that said Letters Patent is hereby corrected as shown below:

In the Specification

Under the heading GOVERNMENT SUPPORT, at Column 1, Line 16, please delete "Contract Nos. GM31749 and 5R01AI074233 both" and insert -- GM031749 and 5R01AI074233 -- therefor.

Signed and Sealed this
Twenty-third Day of December, 2025

John A. Squires
*Director of the United States Patent and Trademark Office*